United States Patent [19]
Bilodeau et al.

[11] Patent Number: 6,162,804
[45] Date of Patent: Dec. 19, 2000

[54] TYROSINE KINASE INHIBITORS

[75] Inventors: Mark T. Bilodeau, Lansdale; April M. Cunningham, Green Lane; Randall W. Hungate, Lansdale; Timothy J. Koester, Lafayette, all of Pa.

[73] Assignee: Merck & Co., Inc., Rahway, N.J.

[21] Appl. No.: 09/266,331

[22] Filed: Mar. 11, 1999

Related U.S. Application Data

[63] Continuation-in-part of application No. 09/143,881, Aug. 31, 1998, abandoned.
[60] Provisional application No. 60/060,151, Sep. 26, 1997.
[51] Int. Cl.$^7$ .................. A61K 31/506; A61K 31/4184; A61K 31/4545; C07D 401/14; C07D 403/14; C07D 413/14
[52] U.S. Cl. .................. 514/234.5; 514/252.19; 514/253.09; 514/274; 514/318; 514/322; 514/339; 514/394; 544/124; 544/139; 544/315; 544/316; 544/364; 544/370; 544/365; 546/193; 546/194; 546/199; 546/273.4; 548/309.7; 548/310.1; 548/310.4; 548/310.7; 548/302.7
[58] Field of Search .................. 548/309.7, 310.1, 548/310.4, 310.7, 302.7; 514/394, 318, 322, 234.5, 253, 274, 253.09, 252.19; 546/193, 194, 199; 544/139, 124, 370, 364, 315

[56] References Cited

U.S. PATENT DOCUMENTS

| | | | |
|---|---|---|---|
| 2,637,731 | 5/1953 | Vaughan, Jr. | 260/296 |
| 3,819,640 | 6/1974 | von Bebenburg | 260/294.8 |
| 4,026,891 | 5/1977 | Austel | 260/250 AH |
| 4,144,341 | 3/1979 | Clark et al. | 424/256 |
| 4,331,671 | 5/1982 | Lesher | 424/263 |
| 4,361,563 | 11/1982 | Austel | 424/250 |
| 4,859,672 | 8/1989 | Spada et al. | 514/254 |
| 4,898,872 | 2/1990 | Campbell | 514/303 |
| 4,971,996 | 11/1990 | Shirashi | 514/521 |
| 5,010,086 | 4/1991 | Lesher et al. | 514/303 |
| 5,066,654 | 11/1991 | Taylor, Jr. | 514/256 |
| 5,360,809 | 11/1994 | Axelsson | 514/338 |
| 5,446,159 | 8/1995 | Stucky et al. | 546/118 |
| 5,501,850 | 3/1996 | Stein | 424/59 |
| 5,514,682 | 5/1996 | Street | 514/266 |
| 5,554,632 | 9/1996 | Teuber | 514/338 |
| 5,593,997 | 1/1997 | Dow et al. | 514/250 |
| 5,637,724 | 6/1997 | Desimone | 548/222 |
| 5,665,709 | 9/1997 | Townsend | 514/43 |
| 5,767,142 | 6/1998 | La Voie | 514/394 |

FOREIGN PATENT DOCUMENTS

| | | |
|---|---|---|
| 385 850 | 9/1990 | European Pat. Off. . |
| 3536030 | 4/1987 | Germany . |
| 7253626 | 10/1995 | Japan . |
| 8183787 | 7/1996 | Japan . |
| 879985 | 3/1986 | U.S.S.R. . |
| 9633192 | 10/1996 | WIPO . |
| 97/02266 | 1/1997 | WIPO . |
| 97/22596 | 6/1997 | WIPO . |
| 97/26258 | 7/1997 | WIPO . |

OTHER PUBLICATIONS

Terman, B.I., Oncogene, vol. 6, pp. 1677–1683, 1991.
Shibuya, M., et al., Oncogent, vol. 5, pp. 519–524, 1990.
Stetsenko, A.V., et al., Chemical Abstract, vol. 78(23), 1973.
Windholz, M., et al., The Merck Index, An Encyclopedia of Chemicals and Drugs, Ninth Edition, p. 141, 1976.
Workman, P., et al., Cancer Biology, vol. 3, pp. 369–381, 1992.

*Primary Examiner*—Evelyn Mei Huang
*Attorney, Agent, or Firm*—J. Antonio Garcia-Rivas; Mark R. Daniel

[57] ABSTRACT

The present invention relates to benzinidazole compounds which inhibit tyrosine kinase enzymes, compositions which contain tyrosine kinase inhibiting compounds and methods of using tyrosine kinase inhibitors to treat tyrosine kinase-dependent diseases/conditions such as angiogenenesis, cancer, atherosclerosis, diabetic retinopathy or autoimmune diseases, in mammals.

21 Claims, No Drawings

TYROSINE KINASE INHIBITORS

This is a continuation in part of U.S. Ser. No. 09/143,881, filed Aug.31, 1998, abandoned, which claims priority to provisional application U.S. Ser. No. 60/060,151, filed Sep. 26, 1997.

BACKGROUND OF THE INVENTION

Tyrosine kinases are a class of enzymes that catalyze the transfer of the terminal phosphate of adenosine triphospate to tyrosine residues in protein substrates. Tyrosine kinases are believed, by way of substrate phosphorylation, to play critical roles in signal transduction for a number of cell functions. Though the exact mechanisms of signal transduction is still unclear, tyrosine kinases have been shown to be important contributing factors in cell proliferation, carcinogenesis and cell differentiation. Accordingly, inhibitors of these tyrosine kinases are useful for the prevention and treatment chemotherapy of proliferative diseases dependent on these enzymes.

For example, a method of treatment described herein relates to neoangiogenesis. Neoangiogenesis occurs in conjunction with tumor growth and in certain diseases of the eye. It is characterized by excessive activity of vascular endothelial growth factor.

Vascular endothelial growth factor (VEGF) binds the high affinity membrane-spanning tyrosine kinase receptors KDR and Flt-1. Cell culture and gene knockout experiments indicate that each receptor contributes to different aspects of angiogenesis. KDR mediates the non-mitogenic function of VEGF whereas Flt-1 appears to modulate mitogenic functions such as those associated with cellular adhesion. Inhibiting KDR thus modulates the level of mitogenic VEGF activity.

Vascular growth in the retina leads to visual degeneration culminating in blindness. VEGF accounts for most of the angiogenic activity produced in or near the retina in diabetic retinopathy. Ocular VEGF MRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells. Viral expression of a VEGF-binding construct of Flk-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological neoangiogenesis, and these are useful in the treatment of diseases in which neoangiogenesis is part of the overall pathology, e.g., diabetic retinal vascularization, as well as various forms of cancer.

Cancers which are treatable in accordance with the present invention demonstrate high levels of gene and protein expression. Examples of such cancers include cancers of the brain, genitourinary tract, lymphatic system, stomach, larynx and lung. These include histiocytic lymphoma, lung adenocarcinoma and small cell lung cancers. Additional examples include cancers in which overexpression or activation of Raf-activating oncogenes (e.g., K-ras, erb-B) is observed. More particularly, such cancers include pancreatic and breast carcinoma.

The present invention relates to compounds which inhibit tyrosine kinase enzymes, compositions which contain tyrosine kinase inhibiting compounds and methods of using tyrosine kinase inhibitors to treat tyrosine kinase-dependent diseases/conditions such as neoangiogenesis, cancer, atherosclerosis, diabetic retinopathy or inflammatory diseases, in mammals.

SUMMARY OF THE INVENTION

A compound is disclosed in accordance with formula Ia:

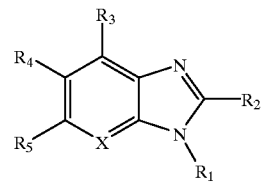

Ia or a pharmaceutically acceptable salt, hydrate or prodrug thereof,
wherein
X is N or C;
$R_1$ & $R_3$ are independently H, $C_{1-10}$ alkyl, $C_{3-6}$ cycloalkyl, $C_{5-10}$ aryl, halo, OH, $C_{3-10}$ heterocyclyl, or $C_{5-10}$ heteroaryl; said alkyl, alkenyl, alkynyl, aryl, heteroaryl and heterocyclyl being optionally substituted with from one to three members selected from $R^a$;
$R_2$ is independently H, $C_{1-6}$ alkyl, $C_{5-10}$ aryl, $C_{3-6}$ cycloalkyl, OH, $NO_2$, —$NH_2$, or halogen;
$R_4$ & $R_5$ are independently H, $C_{1-10}$ alkyl, $C_{3-6}$ cycloalkyl, $C_{1-6}$ alkoxy $C_{2-10}$ alkenyl, $C_{2-10}$ alkynyl, $C_{5-10}$ aryl, $C_{3-10}$ heterocyclyl, $C_{1-6}$ alkoxyNR$_7$R$_8$, halo, $NO_2$, OH, —$NH_2$ or $C_{5-10}$ heteroaryl, said alkyl, alkenyl, alkynyl, aryl, heteroaryl and heterocyclyl being optionally substituted with from one to three members selected from $R^a$, or $R_4$ and $R_5$ can be taken together to form a heterocyclic 5–10 membered saturated or unsaturated ring containing one to three additional heteroatoms selected from the group consisting of N, O and S, which can be optionally substituted with from one to three members selected from $R^a$.
$R^a$ is H, $C_{1-10}$ alkyl, halogen, $NO_2$, R, NHC$_{1-6}$ alkylR$_9$, OR, —NR, RNR$_7$R$_8$, NR$_7$R$_8$, R$_7$R$_8$, CN, $C_{5-10}$ aryl, $C_{5-10}$ heteroaryl or $C_{3-10}$ heterocyclyl;

R is H, $C_{1-6}$ alkyl or $C_{1-6}$ alkyl$R_9$;

$R_9$ is $C_{5-10}$ aryl, $C_{3-10}$ heterocyclyl, or $C_{5-10}$ heteroaryl said aryl, heteroaryl and heterocyclyl being optionally substituted with from one to three members selected from $R^a$; and $R_7$ & $R_8$ are independently H, $C_{1-10}$ alkyl, $C_{3-6}$ cycloalkyl, COR, $C_{5-10}$ aryl, $C_{3-10}$ heterocyclyl, or $C_{5-10}$ heteroaryl, said alkyl, aryl, heteroaryl and heterocyclyl being optionally substituted with from one to three members selected from $R^a$ or $NR_7R_8$ can be taken together to form a heterocyclic 5–10 membered saturated or unsaturated ring containing, in addition to the nitrogen atom, one to two additional heteroatoms selected from the group consisting of N, O and S.

Further compounds are disclosed in accordance with formula I:

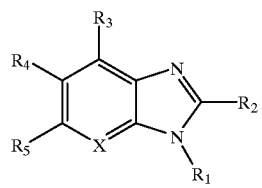

or a pharmaceutically acceptable salt, hydrate or prodrug thereof, wherein

X is N or C;

$R_1$ is H, $C_{1-10}$ alkyl, $C_{3-6}$ cycloalkyl, $C_{5-10}$ aryl, halo, OH, $C_{3-10}$ heterocyclyl, or $C_{5-10}$ heteroaryl; said alkyl, alkenyl, alkynyl, aryl, heteroaryl and heterocyclyl being optionally substituted with from one to three members selected from $R^a$;

$R_2$ & $R_3$ are independently H, $C_{1-6}$ alkyl, $C_{5-10}$ aryl, $C_{3-6}$ cycloalkyl, OH, $N_2$, —$NH_2$, or halogen;

$R_4$ is H, $C_{1-10}$ alkyl, $C_{3-6}$ cycloalkyl, $C_{1-6}$ alkoxy $C_{2-10}$ alkenyl, $C_{2-10}$ alkynyl, $C_{5-10}$ aryl, $C_{3-10}$ heterocyclyl, $C_{1-6}$ alkoxy$NR_7R_8$, $NO_2$, OH, —$NH_2$ or $C_{5-10}$ heteroaryl, said alkyl, alkenyl, alkynyl, aryl, heteroaryl and heterocyclyl being optionally substituted with from one to three members selected from $R^a$;

$R_5$ is H, or $C_{1-6}$ alkyl, OR, halo, $NH_2$ or $NO_2$;

$R^a$ is H, $C_{1-10}$ alkyl, halogen, $NO_2$, OR, —NR, $NR_7R_8$, $R_7R_8$, $C_{5-10}$ aryl, $C_{5-10}$ heteroaryl or $C_{3-10}$ heterocyclyl;

R is H, or $C_{1-6}$ alkyl, $C_{1-6}$ alkyl$R_9$;

$R_9$ is $C_{5-10}$ aryl, $C_{3-10}$ heterocyclyl, or $C_{5-10}$ heteroaryl; and $R_7$ & $R_8$ are independently H, $C_{1-10}$ alkyl, $C_{3-6}$ cycloalkyl, COR, $C_{5-10}$ aryl, $C_{3-10}$ heterocyclyl, or $C_{5-10}$ heteroaryl or $NR_7R_8$ can be taken together to form a heterocyclic 5–10 membered saturated or unsaturated ring containing, in addition to the nitrogen atom, one to two additional heteroatoms selected from the group consisting of N, O and S.

Also disclosed is a pharmaceutical composition which is comprised of a compound represented by the formula I:

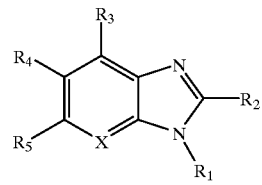

wherein $R_1$, $R_2$, $R_3$, $R_4$ and $R_5$ are described as above or a pharmaceutically acceptable salt or hydrate or prodrug thereof in combination with a carrier.

Also included is a method of treating or preventing a tyrosine kinase dependent disease or condition in a mammal which comprises administering to a mammalian patient in need of such treatment a tyrosine kinase dependent disease or condition treating amount of a compound of formula I or a pharmaceutically acceptable salt, hydrate or pro-drug thereof.

Also included is a method of treating or preventing cancer in a mammalian patient in need of such treatment which is comprised of admininstering to said patient an anti-cancer effective amount of a compound of formula I or a pharmaceutically acceptable salt, hydrate or pro-drug thereof.

Also included in the present invention is a method of treating or preventing diseases in which neoangiogenesis is implicated, which is comprised of administering to a mammalian patient in need of such treatment a compound of formula I or a pharmaceutically acceptable salt, hydrate or pro-drug thereof in an amount which is effective for reducing neoangiogenesis.

More particularly, a method of treating or preventing ocular disease in which neoangiogenesis occurs is included herein, which is comprised of administering to a mammalian patient in need of such treatment a compound of formula I or a pharmaceutically acceptable salt hydrate or pro-drug thereof in an amount which is effective for treating said ocular disease.

More particularly, a method of treating or preventing retinal vascularization is included herein, which is comprised of administering to a mammalian patient in need of such treatment a compound of formula I or a pharmaceutically acceptable salt, hydrate or pro-drug thereof in an amount which is effective for treating retinal vascularization. Diabetic retinopathy is an example of a disease in which neoangiogenesis or retinal vascularization is part of the overall disease etiology. Also included is a method of treating or preventing age-related macular degeneration.

These and other aspects of the invention will be apparent from the teachings contained herein.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopropyl, cyclobutyl, cycloheptyl, cyclopentyl and cyclohexyl.

Alkyl also includes a straight or branched alkyl group which contains or is interrupted by a cycloalkylene portion. Examples include the following:

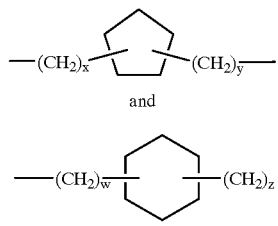

herein: x plus y=from 0–10; and w plus z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups of $R^a$, described herein.

The term "alkenyl" refers to a hydrocarbon radical straight, branched or cyclic containing from 2 to 10 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted with one to three groups of $R^a$, when a substituted alkenyl group is provided.

The term "alkynyl"=0 refers to a hydrocarbon radical straight, branched or cyclic, containing from 2 to 10 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted with 1–3 groups of $R^a$, when a substituted alkynyl group is provided.

Aryl refers to 6–10 membered aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted with 1–3 groups of $R^a$ as defined herein. Preferred substituted aryls include phenyl and naphthyl substituted with one or two groups.

The term heterocycle, heteroaryl, heterocyclyl or heterocyclic, as used herein except where noted, represents a stable 5- to 7-membered mono- or bicyclic or stable 7–10-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. The heterocycle, heteroaryl or heterocyclic may be substituted with 1–3 groups of $R^a$. Examples of such heterocyclic elements, inclusive of all possible isomers, include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyrmidonyl, pyridinonyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thiophenyl, imidazopyridinyl, tetrazolyl, triazinyl, thienyl, benzothienyl, thiamorpholinyl sulfoxide, thiamorpholinyl sulfone, and oxadiazolyl.

The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

The term "prodrug" refers to compounds which are drug precursors which, following administration and absorption, release the drug in vivo via some metabolic process. Exemplary prodrugs include acyl amides of the amino compounds of this inventon such as amides of alkanoic($C_{1-6}$)acids, amides of aryl acids (e.g., benzoic acid) and alkane($C_{1-6}$) dioic acids.

Tyrosine kinase dependent diseases or conditions refers to hyperproliferative disorders which are initiated/maintained by aberrant tyrosine kinase enzyme activity. Examples include psoriasis, cancer, immunoregulation (graft rejection), atherosclerosis, rheumatoid arthritis, angiogenesis (e.g. tumor growth, diabetic retinopathy), etc.

One embodiment of the present invention is in accordance with formula Ia:

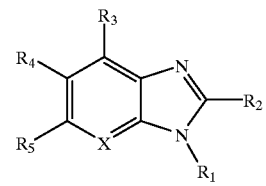

Ia or a pharmaceutically acceptable salt, hydrate or prodrug thereof,
wherein
  X is N or C;
  $R_1$ & $R_3$ are independently H, $C_{1-10}$ alkyl, $C_{3-6}$ cycloalkyl, $C_{5-10}$ aryl, halo, OH, $C_{3-10}$ heterocyclyl, or $C_{5-10}$ heteroaryl; said alkyl, alkenyl, alkynyl, aryl, heteroaryl and heterocyclyl being optionally substituted with from one to three members selected from $R^a$;
  $R_2$ is independently H, $C_{1-6}$ alkyl, $C_{5-10}$ aryl, $C_{3-6}$ cycloalkyl, OH, $NO_2$, $-NH_2$, or halogen;
  $R_4$ & $R_5$ are independently H, $C_{1-10}$ alkyl, $C_{3-6}$ cycloalkyl, $C_{1-6}$ alkoxy $C_{2-10}$ alkenyl, $C_{2-10}$ alkynyl, $C_{5-10}$ aryl, $C_{3-10}$ heterocyclyl, $C_{1-6}$ alkoxyNR$_7$R$_8$, halo, $NO_2$, OH, $-NH_2$ or $C_{5-10}$ heteroaryl, said alkyl, alkenyl, alkynyl, aryl, heteroaryl and heterocyclyl being optionally substituted with from one to three members selected from $R^a$, or $R_4$ and $R_5$ can be taken together to form a heterocyclic 5–10 membered saturated or unsaturated ring containing one to three additional heteroatoms selected from the group consisting of N, O and S, which can be optionally substituted with from one to three members selected from $R^a$.

$R^a$ is H, $C_{1-10}$ alkyl, halogen, $NO_2$, R, $NHC_{1-6}$ alkyl$R_9$, OR, —NR, $RNR_7R_8$, $NR_7R_8$, $R_7R_8$, CN, $C_{5-10}$ aryl, $C_{5-10}$ heteroaryl or $C_{3-10}$ heterocyclyl;

R is H, $C_{1-6}$ alkyl or $C_{1-6}$ alkyl$R_9$;

$R_9$ is $C_{5-10}$ aryl, $C_{3-10}$ heterocyclyl, or $C_{5-10}$ heteroaryl said aryl, heteroaryl and heterocyclyl being optionally substituted with from one to three members selected from $R^a$; and $R_7$ & $R_8$ are independently H, $C_{1-10}$ alkyl, $C_{3-6}$ cycloalkyl, COR, $C_{5-10}$ aryl, $C_{3-10}$ heterocyclyl, or $C_{5-10}$ heteroaryl, said alkyl, aryl, heteroaryl and heterocyclyl being optionally substituted with from one to three members selected from $R^a$ or $NR_7R_8$ can be taken together to form a heterocyclic 5–10 membered saturated or unsaturated ring containing, in addition to the nitrogen atom, one to two additional heteroatoms selected from the group consisting of N, O and S.

An aspect of this invention is described wherein X is C and all other variables are as described above.

Another aspect of this invention is described wherein X is N and all other variables are as described above.

Still another aspect of this invention is described wherein $R_4$ is $C_{1-10}$ alkyl, $C_{3-6}$ cycloalkyl, $C_{5-10}$ aryl, $C_{5-10}$ heteroaryl, or $C_{3-10}$ heterocyclyl, said alkyl, aryl, heteroaryl and heterocyclyl being optionally substituted with from one to three members selected from $R^a$ and all other variables are as described above.

In yet another aspect, the invention is described wherein $R_1$ is $C_{1-10}$ alkyl, $C_{5-10}$ aryl, $C_{3-10}$ heterocyclyl, or C5–10 heteroaryl, said alkyl, aryl, heteroaryl and heterocyclyl being optionally substituted with from one to three members selected from $R^a$ and all other variables are as described above.

Another aspect of this invention is described wherein $R^a$ is H. $C_{1-10}$ alkyl, halogen, $C_{1-6}$ alkyl$R_9$, CN, R, OR, NR, $RNR_7R_8$, $NR_7R_8$, $R_7R_8$ and all other variables are as described above.

A preferred subset of compounds of the present invention is realized when:

$R_1$ & $R_3$ are independently H, $C_{1-10}$ alkyl, $C_{5-10}$ aryl, $C_{3-10}$ heterocyclyl, or $C_{5-10}$ heteroaryl; said alkyl, aryl, heteroaryl and heterocyclyl being optionally substituted with from one to three members selected from $R^a$;

$R_2$ is independently H, $C_{1-6}$ alkyl, $C_{3-6}$ cycloalkyl, OH, or halogen;

$R_4$ & $R_5$ are independently H, $C_{1-10}$ alkyl $C_{3-6}$ cycloalkyl, $C_{5-10}$ aryl, $C_{5-10}$ heteroaryl, $C_{3-10}$ heterocyclyl, $C_{1-6}$ alkoxy$NR_7R_8$, $NO_2$, OH, —$NH_2$ or said alkyl, aryl, heteroaryl and heterocyclyl being optionally substituted with from one to three members selected from $R^a$; and all other variables are as described above.

Another preferred subset of compounds of the present invention is realized when:

$R_1$ & $R_3$ are independently $C_{5-10}$ aryl, $C_{3-10}$ heterocyclyl, or $C_{5-10}$ heteroaryl; said aryl, heteroaryl and heterocyclyl being optionally substituted with from one to three members selected from $R^a$;

$R_2$ is H or $C_{1-6}$ alkyl;

$R_4$ is piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyrimidonyl, pyridinonyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thiophenyl, imidazopyridinyl, tetrazolyl, triazinyl, thienyl, benzothienyl, thiamorpholinyl sulfoxide, thiamorpholinyl sulfone, and oxadiazolyl optionally substituted with from one to three members selected from $R^a$; and all other variables are as described above.

Another embodiment of the invention is a compound in accordance with formula I:

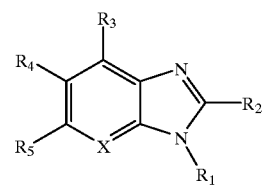

X is N or C;

$R_1$ is H, $C_{1-10}$ alkyl, $C_{5-10}$ aryl, $C_{3-10}$ heterocyclyl, or $C_{5-10}$ heteroaryl; said alkyl, aryl, heteroaryl and heterocyclyl being optionally substituted with from one to three members selected from $R^a$;

$R_2$ & $R_3$ are independently H, $C_{1-6}$ alkyl, OH, $NO_2$, —$NH_2$, or halogen;

$R_4$ is $C_{5-10}$ aryl, $C_{3-10}$ heterocyclyl, $C_{1-6}$ alkoxy$NR_7R_8$, or $C_{5-10}$ heteroaryl, said alkyl, alkenyl, alkynyl, aryl, heteroaryl and heterocyclyl being optionally substituted with from one to three members selected from $R^a$;

$R_5$ is H. $C_{1-6}$ alkyl, OR, halo, NH2 or $NO_2$; $R^a$ is H, $C_{1-10}$ alkyl, halogen, $NO_2$, R, OR, —NR, $NR_7R_8$, $R_7R_8$, $C_{5-10}$ aryl, $C_{5-10}$ heteroaryl or $C_{3-10}$ heterocyclyl, R is H, or $C_{1-6}$ alkyl, $C_{1-6}$ alkyl$R_9$;

$R_9$ is $C_{5-10}$ aryl, $C_{3-10}$ heterocyclyl, or $C_{5-10}$ heteroaryl; and $R_7$ & $R_8$ are independently H, $C_{1-10}$ alkyl, $C_{3-6}$ cycloalkyl, COR, $C_{5-10}$ aryl, $C_{3-10}$ heterocyclyl, or $C_{5-10}$ heteroaryl or $NR_7R_8$ can be taken together to form a heterocyclic 5–10 membered saturated or unsaturated ring containing, in addition to the nitrogen atom, one to two additional heteroatoms selected from the group consisting of N, O and S.

An aspect of this invention is described wherein X is C and all other variables are as described above.

Another aspect of this invention is described wherein X is N and all other variables are as described above.

Still another aspect of this invention is described wherein $R_4$ is $C_{1-10}$ alkyl, $C_{3-6}$ cycloalkyl, $C_{5-10}$ aryl, $C_{5-10}$ heteroaryl, or $C_{3-10}$ heterocyclyl, said alkyl, aryl, heteroaryl and heterocyclyl being optionally substituted with from one to three members selected from $R^a$ and all other variables are as described above.

In yet another aspect, the invention is described wherein $R_1$ is $C_{1-10}$ alkyl, $C_{5-10}$ aryl, $C_{3-10}$ heterocyclyl, or $C_{5-10}$ heteroaryl, said alkyl, aryl, heteroaryl and heterocyclyl being optionally substituted with from one to three members selected from $R^a$ and all other variables are as described above.

A preferred embodiment of this invention is realized when:

$R_1$ is H, $C_{1-10}$ alkyl, $C_{5-10}$ aryl, $C_{3-10}$ heterocyclyl, or $C_{5-10}$ heteroaryl; said alkyl, aryl, heteroaryl and heterocyclyl being optionally substituted with from one to three members selected from $R^a$;

$R_2$ & $R_3$ are independently H, $C_{1-6}$ alkyl, $C_{3-6}$ cycloalkyl, OH, or halogen;

$R_4$ is H, $C_{1-10}$ alkyl, $C_{3-6}$ cycloalkyl, $C_{5-10}$ aryl, $C_{5-10}$ heteroaryl, $C_{3-10}$ heterocyclyl, $C_{1-6}$ alkoxyNR$_7$R$_8$, NO$_2$, OH, —NH$_2$ or said alkyl, aryl, heteroaryl and heterocyclyl being optionally substituted with from one to three members selected from $R^a$; and all other variables are as described above.

Another preferred embodiment of this invention is realized when:

$R_1$ is $C_{5-10}$ aryl, $C_{3-10}$ heterocyclyl, or $C_{5-10}$ heteroaryl; said aryl, heteroaryl and heterocyclyl being optionally substituted with from one to three members selected from $R^a$;

$R_2$ & $R_3$ are independently H or $C_{1-6}$ alkyl;

$R_4$ is $C_{1-10}$ alkyl, $C_{5-10}$ aryl, $C_{5-10}$ heteroaryl, $C_{3-10}$ heterocyclyl said alkyl, aryl, heteroaryl and heterocyclyl being optionally substituted with from one to three members selected from $R^a$; and all other variables are as described above.

Still another embodiment of the invention is a compound in accordance with formula IIa:

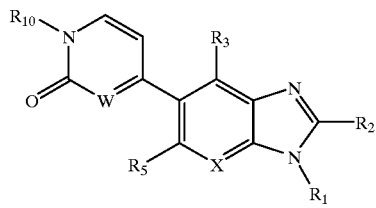

IIa or a pharmaceutically acceptable salt, hydrate or prodrug thereof, wherein

X & W are independently N or C;

$R_1$ & $R_3$ are independently H, $C_{1-10}$ alkyl, $C_{3-6}$ cycloalkyl, $C_{5-10}$ aryl, halo, OH, $C_{3-10}$ heterocyclyl, or $C_{5-10}$ heteroaryl; said alkyl, alkenyl, allynyl, aryl, heteroaryl and heterocyclyl being optionally substituted with from one to three members selected from $R^a$;

$R_2$ is independently H, $C_{1-6}$ alkyl, $C_{5-10}$ aryl, $C_{3-6}$ cycloalkyl, OH, NO$_2$, —NH$_2$, or halogen;

$R_5$ is independently H, $C_{1-10}$ alkyl, $C_{3-6}$ cycloalkyl, $C_{1-6}$ alkoxy $C_{2-10}$ alkenyl, $C_{2-10}$ alkynyl, $C_{5-10}$ aryl, $C_{3-10}$ heterocyclyl, $C_{1-6}$ alkoxyNR$_7$R$_8$, halo, NO$_2$, OH, —NH$_2$ or $C_{5-10}$ heteroaryl, said alkyl, alkenyl, alkynyl, aryl, heteroaryl and heterocyclyl being optionally substituted with from one to three members selected from $R^a$;

$R_{10}$ is H, or $C_{1-6}$ alkyl, $C_{1-6}$ alkylR$_9$, $C_{5-10}$ aryl, $C_{3-10}$ heterocyclyl, NHC$_{1-6}$ alkylR$_9$, said alkyl (where R is $C_{1-6}$ alkyl), aryl, heteroaryl and heterocyclyl being optionally substituted with from one to three members selected from $R^a$;

$R^a$ is H, $C_{1-10}$ alkyl, halogen, NO$_2$, OR, —NR, RNR$_7$R$_8$, NR$_7$R$_8$, R$_7$R$_8$, CN, $C_{5-10}$ aryl, $C_{5-10}$ heteroaryl or $C_{3-10}$ heterocyclyl;

R is H, $C_{1-6}$ alkyl or $C_{1-6}$ alkylR$_9$;

$R_9$ is $C_{5-10}$ aryl, $C_{3-10}$ heterocyclyl, or $C_{5-10}$ heteroaryl said aryl, heteroaryl and heterocyclyl being optionally substituted with from one to three members selected from $R^a$; and $R_7$ & $R_8$ are independently H, $C_{1-10}$ alkyl, $C_{3-6}$ cycloalkyl, COR, $C_{5-10}$ aryl, $C_{3-10}$ heterocyclyl, or $C_{5-10}$ heteroaryl, said alkyl, aryl, heteroaryl and heterocyclyl being optionally substituted with from one to three members selected from $R^a$ or NR$_7$R$_8$ can be taken together to form a heterocyclic 5–10 membered saturated or unsaturated ring containing, in addition to the nitrogen atom, one to two additional heteroatoms selected from the group consisting of N, O and S.

An aspect of this invention is described wherein X or W independently are C and all other variables are as described above.

Another aspect of this invention is described wherein X or W are independently N and all other variables are as described above.

Still another aspect of this invention is described wherein $R_{10}$ is H, $C_{1-6}$ alkyl, $C_{1-6}$ alkylR$_9$, $C_{5-10}$ aryl, $C_{5-10}$ heteroaryl, or $C_{3-10}$ heterocyclyl, said alkyl, aryl, heteroaryl and heterocyclyl being optionally substituted with from one to three members selected from $R^a$ and all other variables are as described above.

Examples of the compounds of this invention are:

1) 1-phenyl-5-(4-methoxyphenyl)benzimidazole,
2) 1-phenyl-5-(4-(2-(1-piperidinyl)ethoxy)phenyl) benzimidazole,
3) 3-phenyl-6-(4-methoxylphenyl)imidazo[4, 5-b] pyridine,
4) 3-phenyl-6-(4-(2-(1-piperidinyl)ethoxy)phenyl) imidazo[4,5-b]pyridine,
5) 3-phenyl-6-(4-(2-(1-piperidinyl)ethoxyphenyl)imidazo [4,5-b]pyridine,
6) 3-(2-thiazoyl)-6-(4-(3-(1-piperidinyl)propylphenyl) imidazo[4,5-]pyridine,
7) 1-(2-thiazoyl)-5-(4-(3-(1-piperidinyl)propyl)phenyl) benzimidazole,
8) 1-(3-thiophenyl)-5-(4-(3-(1-piperidinyl)propyl) phenyl)imidazo[4,5-b]pyridine,
9) 1-(3-thiophenyl)-5-(4-(3-(1-piperidinyl)propyl) phenyl)benzimidazole,
10) 3-(3-thiophenyl)-6-(4-(3-(1-piperidinyl) propylphenyl)imidazo[4,5-b]pyridine,
11) 1-Phenyl-5-[5-(2-piperidin-1-yl-ethoxy)-pyridin-2-yl] -1H-benzimidazole,
12) 1-(4-Cyanophenyl)-5-[6-(2-piperidin-1-yl-ethoxy)-pyridin-3-yl]-1H-benzimidazole,
13) 1-Phenyl-5-[6-(2-piperidin-1-yl-ethoxy)-pyridin-3-yl]-1H-benzimidazole,
14) 1-(3-Cyanophenyl)-5-[6-(2-piperidin-1-yl-ethoxy)-pyridin-3-yl]-1H-benzimidazole,
15) 1-(3-Thiophene)-5-[6-(2-piperidin-1-yl-ethoxy)-pyridin-3-yl]-1H-benzimidazole,
16) [5-(1-Phenyl-1H-benzoimidazol-5-yl)-pyridin-2-yl] -(2-piperidin-1-yl-ethyl)-amine,
17) [5-(1-Phenyl-1H-benzoimidazol-5-yl)-pyridin-2-yl]-(2-morpholin-1-yl-ethyl)-amine,
18) 1-(3-Pyridyl)-5-(4-(2-(1-piperidinyl)ethoxy)phenyl) benzimidazole,
19) 4-(1-phenyl-1H-benzoimidazol-5-yl)-1-(3-piperidin-1-yl-propyl)-1H-pyridin-2-one, 20) 4-(1-phenyl-1H-benzoimidazol-5-yl)-1-(3-piperidin-1-yl-ethyl)-1H-pyridin-2-one,
21) 1-(2-morpholin-4-yl-ethyl)-4-(1-phenyl-1H-benzoimidazol-5-yl)-1H-pyridin-2-one,
22) 1-(3-dimethylamino-propyl)-4-(1-phenyl-1H-benzoimidazol-5-yl)-1H-pyridin-2-one,
23) 1-(1-methyl-piperidin-3-ylmethyl)-4-(1-phenyl-1H-benzoimidazol-5-yl)-1H-pyridin-2-one,
24) 1-[3-(4-methylpiperazin-1-yl)-propyl] -4-(1-phenyl-1H-benzoimidazol-5-yl)-1H-pyridin-2-one,
25) 1-(2-dimethylamino-propyl)-4-(1-phenyl-1H-benzoimidazol-5-yl)-1H-pyridin-2-one,
26) 1-(3-dimethylamino-2-methyl-propyl)-4-(1-phenyl-1H-benzoimidazol-5-yl)-1H-pyridin-2-one,
27) 1- [2-(4-cyano-piperidin-1-yl)-ethyl]-4-(1-phenyl-1H-benzoimidazol-5-yl)-1H-pyridin-2-one,
28) 1-(3-piperidin-1-yl-propyl)-4-(1-thiophen-3-yl-1H-benzoimidazol-5-yl)-1H-pyridin-2-one,
29) 1-(3-piperidin-1-yl-ethyl)-4-(1-thiophen-3-yl-1H-benzoimidazol-5-yl)-1H-pyridin-2-one,
30) 1-(2-morpholin-4-yl-ethyl)-4-(1-thiophen-3-yl-1H-benzoimidazol-5-yl)-1H-pyridin-2-one,
31) 1-(3-dimethylamino-propyl)-4-(1-thiophen-3-yl-1H-benzoimidazol-5-yl)-1H-pyridin-2-one,
32) 1-(1-methyl-piperidin-3-ylmethyl)-4-(1-thiophen-3-yl-1H-benzoimidazol-5-yl)-1H-pyridin-2-one,
33) 1-[3-(4-methylpiperazin-1-yl)-propyl] -4-(1-thiophen-3-yl-1H-benzoimidazol-5-yl)-1H-pyridin-2-one,
34) 1-(2-dimethylarnino-propyl)-4-(1-thiophen-3-yl-1H-benzoimidazol-5-yl)-1H-pyridin-2-one,
35) 1-(3-dimethylamino-2-methyl-propyl)-4-(1-thiophen-3-yl-1H-benzoimidazol-5-yl)-1H-pyridin-2-one,
36) 1- [2-(4-cyano-piperidin-1-yl)-ethyl]-4-(1-thiophen-3-yl-1H-benzoimidazol-5-yl)-1H-pyridin-2-one,
37) 5-(1-phenyl-1H-benzoimidazol-5-yl)-1-(3-piperidin-1-yl-propyl)-1H-pyridin-2-one,
38) 5-(1-phenyl-1H-benzoimidazol-5-yl)-1-(3-piperidin-1-yl-ethyl)-1H-pyridin-2-one,
39) 1-(2-morpholin-4-yl-ethyl)-5-(1-phenyl- I H-benzoimidazol-5-yl)-1H-pyridin-2-one,
40) 1-(3-dimethylamino-propyl)-5-(1-phenyl-1H-benzoimidazol-5-yl)-1H-pyridin-2-one,
41) 1-(1-methyl-piperidin-3-ylmethyl)-5-(1-phenyl-1H-benzoimidazol-5-yl)-1H-pyridin-2-one,
42) 1-[3-(4-methylpiperazin-1-yl)-propyl)]-5-(1-phenyl-1H-benzoimidazol-5-yl)-1H-pyridin-2-one,
43) 1-(2-dimethylamino-propyl)-5-(1-phenyl-1H-benzoimidazol-5-yl)-1H-pyridin-2-one,
44) 1-(3-dimethylamino-2-methyl-propyl)-5-(1-phenyl-1H-benzoimidazol-5-yl)-1H-pyridin-2-one,
45) 1-[2-(4-cyano-piperidin-1-yl)-ethyl]-5-(1-phenyl-1H-benzoimidazol-5-yl)-1H-pyridin-2-one,
46) 1-(3-piperidin-1-yl-propyl)-5-(1-thiophen-3-yl-1H-benzoimidazol-5-yl)-1H-pyridin-2-one,
47) 1-(3-piperidin-1-yl-ethyl)-5-(1-thiophen-3-yl-1H-benzoirnidazol-5-yl)-1H-pyridin-2-one,
48) 1-(2-morpholin-4-yl-ethyl)-5-(1-thiophen-3-yl-1H-benzoimidazol-5-yl)-1H-pyridin-2-one,
49) 1-(3-dimethylamino-propyl)-5-(1-thiophen-3-yl-1H-benzoimidazol-5-yl)-1H-pyridin-2-one,
50) 1-(1-methyl-piperidin-3-ylmethyl)-5-(1-thiophen-3-yl-1H-benzoimidazol-5-yl)-1H-pyridin-2-one,
51) 1-[3-(4-methylpiperazin-1-yl)-propyl)]-5-(1-thiophen-3-yl-1H-benzoimidazol-5-yl)-1H-pyridin-2-one,
52) 1-(2-dimethylamino-propyl)-5-(1-thiophen-3-yl-1H-benzoimidazol-5-yl)-1H-pyridin-2-one,
53) 1-(3-dimethylamino-2-methyl-propyl)-5-(1-thiophen-3-yl-1H-benzoimidazol-5-yl)-1H-pyridin-2-one,
54) 1- [2-(4-cyano-piperidin-1-yl)-ethyl]-5-(1-thiophen-3-yl-1H-benzoimidazol-5-yl)-1H-pyridin-2-one,
55) 5-(1-phenyl-1H-benzoimidazol-5-yl)-1-(3-piperidin-1-yl-propyl)-1H-pyrimidin-2-one,
56) 5-(1-phenyl-1H-benzoimidazol-5-yl)-1-(3-piperidin-1-yl-ethyl)-1H-pyrimidin-2-one,
57) 1-(2-morpholin-4-yl-ethyl)-5-(1-phenyl-1H-benzoimidazol-5-yl)-1H-pyrimidin-2-one,
58) 1-(3-dimethylamino-propyl)-5-(1-phenyl-1H-benzoinidazol-5-yl)-1H-pyrimidin-2-one,
59) -(1-methyl-piperidin-3-ylmethyl)-5-(1-phenyl-1H-benzoimidazol-5-yl)-1H-pyrimidin-2-one,
60) 1-[3-(4-methylpiperazin-1-yl)-propyl)]-5-(1-phenyl-1H-benzoimidazol-5-yl)-1H-pyrimidin-2-one,
61) 1-(2-dirnethylamino-propyl)-5-(1-phenyl-1H-benzoimidazol-5-yl)-1H-pyrimidin-2-one,
62) 1-(3-dimethylamino-2-methyl-propyl)-5-(1-phenyl-1H-benzoimidazol-5-yl)-1H-pynmidin-2-one,
63) 1-[2-(4-cyano-piperidin-1-yl)-ethyl]-5-(1-phenyl-1H-benzoimidazol-5-yl)-1H-pyrimidin-2-one,
64) 1-(3-piperidin-1-yl-propyl)-5-(1-thiophen-3-yl-1H-benzoimnidazol-5-yl)-1H-pyrimidin-2-one,
65) 1-(3-piperidin-1-yl-ethyl)-5-(1-thiophen-3-yl-1H-benzoimidazol-5-yl)-1H-pyrimidin-2-one,
66) 1-(2-morpholin-4-yl-ethyl)-5-(1-thiophen-3-yl-1H-benzoimidazol-5-yl)-1H-pyrimidin-2-one,
67) 1-(3-dimethylamino-propyl)-5-(1-thiophen-3-yl-1H-benzoimidazol-5-yl)-1H-pyrimidin-2-one,
68) 1-(1-methyl-piperidin-3-ylmethyl)-5-(1-thiophen-3-yl-1H-benzoimidazol-5-yl)-1H-pyrirnidin-2-one,
69) 1-[3-(4-methylpiperazin-1-yl)-propyl)] -5-(1-thiophen-3-yl-1H-benzoimnidazol-5-yl)-1H-pyrimidin-2-one,
70) 1-(2-dimethylamino-propyl)-5-(1-thiophen-3-yl-1H-benzoimnidazol-5-yl)-1H-pyrimidin-2-one,
71) 1-(3-dimethylamino-2-methyl-propyl)-5-(1-thiophen-3-yl-1H-benzoimidazol-5-yl)-1H-pyrimidin-2-one,
72) 1-[2-(4-cyano-piperidin-1-yl)-ethyl]-5-(1-thiophen-3-yl-1H-benzoimnidazol-5-yl)-1H-pyrimidin-2-one,
73) 4-(1-phenyl-1H-benzoimidazol-5-yl)-1-(3-piperidin-1-yl-propyl)-1H-pyrimidin-2-one,
74) 4-(1-phenyl-1H-benzoimidazol-5-yl)-1-(3-piperidin-1-yl-ethyl)-1H-pyrimidin-2-one,
75) 1-(2-morpholin-4-yl-ethyl)-4-(1-phenyl-1H-benzoimidazol-5-yl)-1H-pyrimidin-2-one,
76) 1-(3-dimnethylamino-propyl)-4-(1-phenyl-1H-benzoimidazol-5-yl)-1H-pyrimidin-2-one,
77) 1-(1-methyl-piperidin-3-ylmethyl)-4-(1-phenyl-1H-benzoimidazol-5-yl)-1H-pyrimidin-2-one,
78) 1-[3-(4-methylpiperazin-1-yl)-propyl)]-4-(1-phenyl-1H-benzoimidazol-5-yl)-1H-pyrimidin-2-one,
79) 1-(2-dimethylamino-propyl)-4-(1-phenyl-1H-benzoimidazol-5-yl)-1H-pyrimidin-2-one,
80) 1-(3-dimethylamino-2-methyl-propyl)-4-(1-phenyl-1H-benzoimidazol-5-yl)-1H-pyrimidin-2-one, 81) 1-[2-(4-cyano-piperidin-1-yl)-ethyl]-4-(1-phenyl-1H-benzoimidazol-5-yl)-1H-pyrimidin-2-one, 82) 1-(3-piperidin-1-yl-propyl)-4-(1-thiophen-3-yl-1H-benzoirmidazol-5-yl)-1H-pyrimidin-2-one 83) 1-(3-piperidin-1-yl-ethyl)-4-(1-thiophen-3-yl-1H-benzoimidazol-5-yl)-1H-pyrimidin-2-one, 84) 1-(2-morpholin-4-yl-ethyl)-4-(1-thiophen-3-yl-1H-benzoimidazol-5-yl)-1H-pyrimidin-2-one, 85) 1-(3-dimethylamino-propyl)-4-(1-thiophen-3-yl-1H-benzoimidazol-5-yl)-1H-pyrimidin-2-one, 86) 1-(1-methyl-piperidin-3-ylmethyl)-4-(1-thiophen-3-yl-1H-benzoimidazol-5-yl)-1H-pyrimidin-2-one, 87) 1-[3-(4-methylpiperazin-1-yl)-propyl)]-4-(1-thiophen-3-yl-1H-benzoimidazol-5-yl)-1H-pyrimidin-2-one, 88) 1-(2-dimethylamino-propyl)-4-(1-thiophen-3-yl-1H-benzoimidazol-5-yl)-1H-pyrimidin-2-one, 89) 1-(3-dimethylamino-2-methyl-propyl)-4-(1-thiophen-3-yl-1H-benzoimidazol-5-yl)-1H-pyrimidin-2-one, 90) 1- [2-(4-cyano-piperidin-1-yl)-ethyl]-4-(1-thiophen-3-yl-1H-benzoimidazol-5-yl)-1H-pyrimidin-2-one, 91) 1-(4-Pyridyl)-5-(4-(2-(1-piperidinyl)ethoxy)phenyl)benzimidazole, 92) 1-(3-Pyridyl)-5-[6-(2-piperidin-1-yl-ethoxy)-pyridin-3-yl]-1H-benzimidazole, and 93) 1-(4-Pyridyl)-5-[6-(2-piperidin-1-yl-ethoxy)-pyridin-3-yl]-1H-benzimidazole or a pharmaceutically acceptable salt, hydrate or prodrug thereof.

The invention described herein includes a pharmaceutical composition which is comprised of a compound of formula I or a pharmaceutically acceptable salt or hydrate thereof in combination with a carrier. As used herein the terms "pharmaceutically acceptable salts" and "hydrates" refer to those salts and hydrated forms of the compound which would be apparent to the pharmaceutical chemist, i.e., those which favorably affect the physical or pharmacokinetic properties of the compound, such as solubility, palatability, absorption, distribution, metabolism and excretion. Other factors, more practical in nature, which are also important in the selection, are the cost of the raw materials, ease of crystallization, yield, stability, solubility, hygroscopicity and flowability of the resulting bulk drug.

When a compound of formula I is present as a salt or hydrate which is non-pharmaceutically acceptable, this can be converted to a salt or hydrate form which is pharmaceutically acceptable in accordance with the present invention.

When the compound is negatively charged, it is balanced by a counterion, e.g., an alkali metal cation such as sodium or potassium. Other suitable counterions include calcium, magnesium, zinc, ammonium, or alkylammonium cations such as tetramethylammonium, tetrabutylammonium, choline, triethylhydroammonium, meglumine, triethanolhydroammonium, etc. An appropriate number of counterions is associated with the molecule to maintain overall charge neutrality. Likewise when the compound is positively charged, e.g., protonated, an appropriate number of negatively charged counterions is present to maintain overall charge neutrality.

Pharmaceutically acceptable salts also include acid addition salts. Thus, the compound can be used in the form of salts derived from inorganic or organic acids or bases. Examples include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quatemized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

The compounds of the present invention, may have asymmetric centers and occur as racemates, racemic mixtures and as individual diastereomers, or enantiomers with all isomeric forms being included in the present invention. When any variable (e.g., aryl, heterocyle, R1, etc)occurs more than one time in any constituent or in Formula I, its definition on each occurrence is independent of its definition at every other occurrence, unless otherwise stated.

The compounds of the invention can be formulated in a pharmaceutical composition by combining the compound with a pharmaceutically acceptable carrier. Examples of such compositions and carriers are set forth below.

The compounds may be employed in powder or crystalline form, in solution or in suspension. They may be administered orally, parenterally (intravenously or intramuscularly), topically, transdermally or by inhalation.

Thus, the carrier employed may be, for example, either a solid or liquid. Examples of solid carriers include lactose, terra alba, sucrose, talc, gelatin, agar, pectin, acacia, magnesium stearate, stearic acid and the like. Examples of liquid carriers include syrup, peanut oil, olive oil, water and the like. Similarly, the carrier for oral use may include time delay material well known in the art, such as glyceryl monostearate or glyceryl distearate alone or with a wax.

Topical applications may be formulated in carriers such as hydrophobic or hydrophilic bases to form ointments, creams, lotions, in aqueous, oleaginous or alcoholic liquids to form paints or in dry diluents to form powders. Such topical formulations can be used to treat ocular diseases as well as inflammatory diseases such as rheumatoid arthritis, psoriasis, contact dermatitis, delayed hypersensitivity reactions and the like.

Examples of oral solid dosage forms include tablets, capsules, troches, lozenges and the like. The size of the dosage form will vary widely, but preferably will be from about 25 mg to about 500 mg. Examples of oral liquid dosage forms include solutions, suspensions, syrups, emulsions, soft gelatin capsules and the like. Examples of injectable dosage forms include sterile injectable liquids, e.g., solutions, emulsions and suspensions. Examples of injectable solids would include powders which are reconstituted, dissolved or suspended in a liquid prior to injection.

In injectable compositions, the carrier is typically comprised of sterile water, saline or another injectable liquid, e.g., peanut oil for intramuscular injections. Also, various buffering agents, preservatives and the like can be included.

For the methods of treatment disclosed herein, dosages can be varied depending upon the overall condition of the patient, the nature of the illness being treated and other factors. An example of a suitable oral dosage range is from about 0.1 to about 80 mg/kg per day, in single or divided doses. An example of a suitable parenteral dosage range is from about 0.1 to about 80 mg/kg per day, in single or divided dosages, administered by intravenous or intramuscular injection. An example of a topical dosage range is from about 0.1 mg to about 150 mg, applied externally from about one to four times a day. An example of an inhalation dosage range is from about 0.01 mg/kg to about 1 mg/kg per day.

The examples which follow illustrate the compounds that can be synthesized but they are not limited by the compounds in the tables nor by any particular substituents employed in the schemes for illustrative purposes.

The compounds may be administered in conventional dosages as a single agent or in combination with other therapeutically active compounds. The non-limiting examples that follow are illustrations of the compounds of the instant invention and are not meant to limit the invention in any way.

EXAMPLE 1

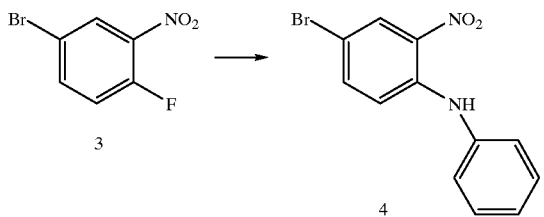

1-Bromo-4-fluoro-3-nitrobenzene (3) (1.14 mL, 9.06 mmol) was dissolved in 5 mL of anhydrous 1-methyl-2-pyrrolidinone under argon. Aniline (0.870 mL, 9.55 mmol) was added followed by the addition of N,N-diisopropylethylamine (1.90 mL, 10.9 mmol) and the resulting solution was heated to 120° C. After 14 h additional aniline (0.082 mL, 0.90 mmol) was added and heating was continued for 8 h. The reaction solution was cooled to ambient temperature, diluted with water and extracted with ethyl acetate (3x). The combined extracts was washed with brine, dried over $Na_2SO_4$, filtered and concentrated in vacuo to provide 4.

$^1$H NMR (CDCl$_3$) δ9.46 (bs, 1H), 8.35 (d, 1H, J=2.4 Hz), 7.45–7.40 (m, 3H), 7.29–7.25 (m, 3H), 7.10 (d, 1H, J=9.2 Hz).

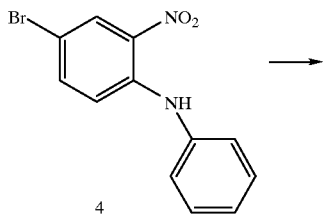

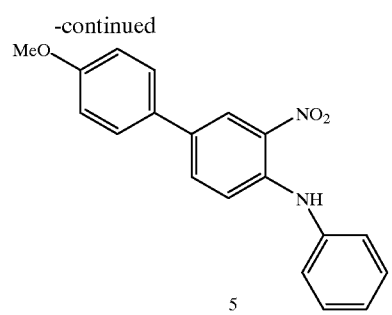

Bromoaromatic 4 (0.218 g, 0.744 mmol) and 4-methoxyboronic acid (0.125 g, 0.823 mmol) were dissolved in a mixture of dioxane (4 mL) and water (3 mL). Sodium carbonate (0.60 g, 5.7 mmol) was added and the resulting mixture was degassed and put under argon. Tetrakis(triphenylphosphine)palladium(0) (0.043 g, 0.037 mmol) was added and the reaction was heated to 80° C. After 14 h the reaction was cooled to ambient temperature, diluted with water and extracted with ethyl actetate (3x). The combined extracts was dried with Na$_2$SO4, filtered and concentrated to dryness. Purification by flash column chromatography (2×16 cm silica gel, 6:1 hexane/ethyl acetate) provided 5.

$^1$H NMR (CDC13) d 9.48 (bs, 1H), 8.40 (d, 1H, J=2.4 Hz), 7.58 (dd, 1H, J=2.4, 9.2 Hz), 7.50 (d, 2H, 9.0 Hz), 7.43 (t, 2H, J=9.0 Hz), 7.32–7.22 (m, 4H), 6.98 (d, 2H, J=9.0 Hz), 3.83 (s, 3H).

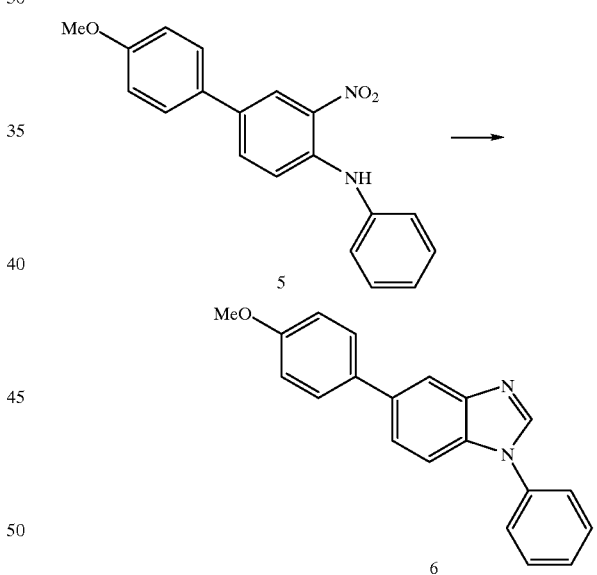

1-phenyl-5-(4-methoxyphenyl)benzimidaole.

Nitroaniline 5 (0.213 g, 0.665 mmol) and palladium on carbon (10%, 100 mg) were stirred in 8 mL 3:1 EtOH/AcOH. The reaction was put under a balloon of H$_2$. After 2 h the reaction was filtered through a plug of celite and the filtrate was concentrated to dryness. The resulting residue was dissolved in 1.5 mL trimethylorthoformate and heated to 120° C. for 30 min. The solution was cooled concentrated to dryness and purified by flash column chromatography (2×15 cm silica gel, 1:1 hexane/ethyl acetate) which provided 6.

$^1$H NMR (CDCl$_3$) δ8.14 (s, 1H), 8.04 (d, 1H, J=0.9 Hz), 7.62–7.50 (m, 8H), 7.48 (t, 1H, J=7.1Hz), 7.01 (d, 2H, J=8.8 Hz), 3.87 (s, 3H); FAB mass spectrometry [M+H]+301.1;

Anal. Calcd. for $C_{20}H_{16}N_2O$: C, 79.98; H, 5.37; N, 9.33. Found: C, 79.71; H, 5.48; N, 9.21.

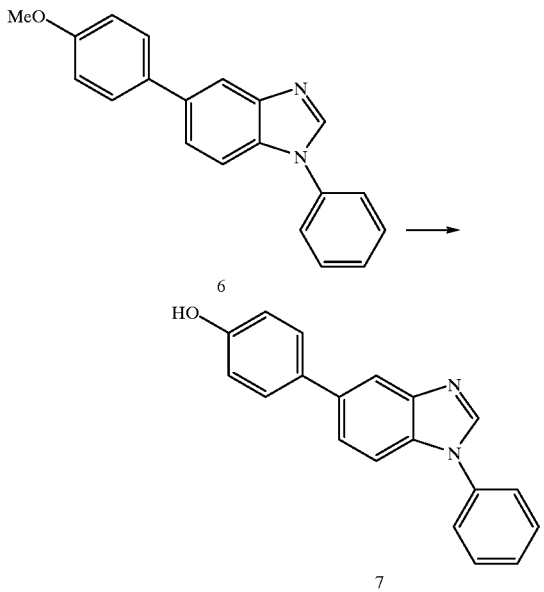

An oven dried flask under argon was charged with benzimidazole 6 (0.039 g, 0.13 mmol), aluminum chloride (0.175 g, 1.31 mmol), and sodium iodide (0.200 g, 1.33 mmol). Anhydrous acetonitrile (1 mL) and dichloromethane (0.5 mL) were added and reaction was heated to reflux. After 44 h the reaction was cooled to ambient temperature, quenched with water and extracted 3 x with ethyl acetate. The combined extracts was dried over $Na_2SO_4$, filtered and concentrated to dryness. The resulting residue was triturated with ether, filtered and dried to provide phenol 7.

$^1$H NMR (CDCl$_3$) δ9.48 (s, 1H), 8.58 (s, 1H), 7.93 (s, 1H), 7.73–7.71 (m, 2H), 7.67–7.63 (m, 3H), 7.57–7.49 (m, 4H), 6.86 (d, 2H, J=8.6 Hz).

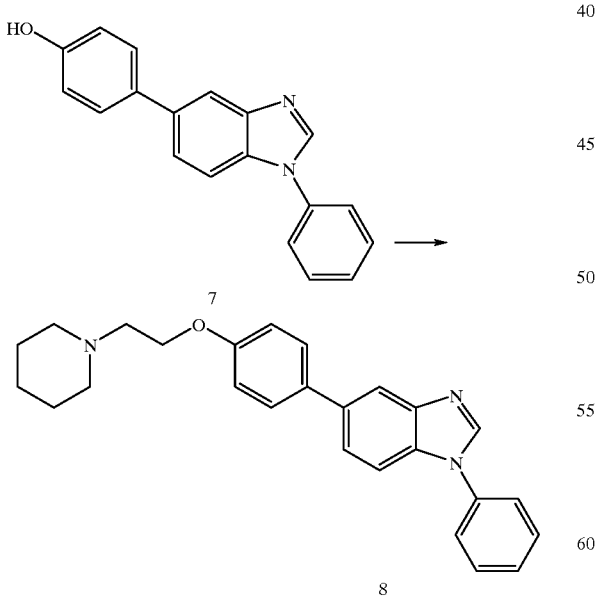

1-phenyl-5-(4-(2-(1-piperidinyl)ethoxy)phenyl) benzimidazole

Benzimidazole 7 (0.025 g, 0.087 mmol) and N-(2-chloroethyl)piperidine hydrochloride (11 mg, 0.059 mmol) were dissolved in anhydrous N,N-dimethylformamide (0.5 mL). Cesuim carbonate (0.085 g, 0.26 mmol) was added and the resulting mixture was heated to 50° C. After 2 h additional and N-(2-chloroethyl)piperidine hydrochloride (11 mg, 0.059 mmol) was added. After 1 h the reaction was allowed to cool, quenched with water and extracted with ethyl acetate (3x). The combined extracts was washed with brine, dried over $eNa_2SO_4$, filtered and concentrated to dryness. Purification by flash column chromatography (2×16 cm silica gel, 9:1 $CH_2Cl_2$/MeOH) provided 8 as a colorless oil.

$^1$H NMR (CDCl$_3$) δ8.14 (s, 1H), 8.03 (d, 1H, J=0.9 Hz), 7.62–7.50 (m, 8H), 7.48 (t, 1H, J=7.2 Hz), 7.01 (d, 2H, J=8.8 Hz), 4.21 (bt, 2H, J=5.3 Hz), 2.87 (bs, 2H), 2.59 (bs, 4H), 1.66 (bs, 4H), 1.48 (bs, 2H); Mass spectrometry [M+H]$^+$ 398.3.

EXAMPLE 2

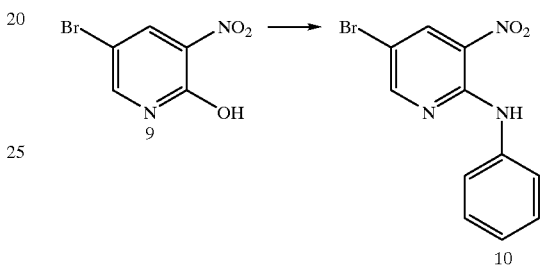

5-Bromo-2-hydroxy-3-nitropyridine (9) (5.736 g, 0.0262 mol) and 15 mL thionyl chloride were added under argon. N,N dimethylformamide (1 mL) was then added and the solution was heated to reflux for 1 hr. By the end of the reaction, the bromohydroxynitropyridine was completely dissolved in solution. After cooling to ambient temperature, 5 mL of toluene was added, and the solution was concentrated under vacuum. The product, 5-bromo-2-chloro-3-nitropyridine, was a yellow crystalline solid.

The bromochloronitropyridine was dissolved in 15 mL of anhydrous 1-methyl-2-pyrrolidinone. Aniline (3.580 mL, 0.0393 mol) was added followed by the addition of ,N -diisopropylethylamine (13.69 ML, 0.0786 mol) and the solution was heated to 120° C. After 1.5 hr., the solution was cooled to ambient temperature and diluted with water. The product was extracted using ethyl acetate and washed with brine. The organic layer was then dried over sodium sulfate, filtered, concentrated, and dried in vacuo. The crude mixture was purified using flash column chromatography (7.5×16 cm silica gel, 10:1 hexane:ethyl acetate) to afford 10.

$^1$H NMR (CDCl$_3$) δ 10.04 (bs, 1H), 8.65 (dd, 1H, J=2.2 Hz), 8.50(dd, 1H, J=2.4 Hz), 7.60 (d, 2H, J=8.6 Hz), 7.40(t, 2H, J=7.5 Hz), 7.21 (t, 1H, J=7.3 Hz).

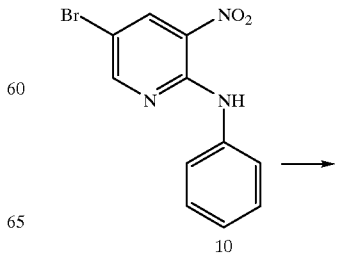

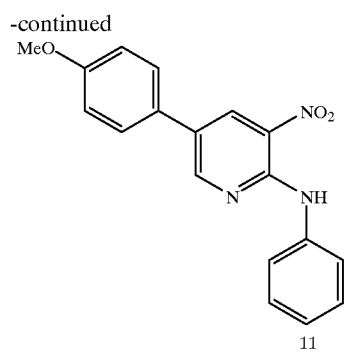

Bromoaromatic 10 (30 mg, 0.102 mmol), 4-methoxyphenylboronic acid (17 mg, 0.112 mmol) was dissolved in 0.75 mL dioxane followed by the addition of 204 μL of 2M sodium carbonate. The vessel was flushed with argon followed by the addition of tetrakis (triphenylphosphine)palladium(0) (6 mg, 0.005 mmol) and 0.56 mL water. The vessel was flushed again with argon and heated to 80 °C. for 2.5 hr. The solution was cooled to room temperature and diluted with water. The product was extracted with ethyl acetate and washed with brine, followed by drying over sodium sulfate. The organic layer was concentrated, and the product dried in vacuo. The crude mixture was purified by flash column chromatography (2.5×8 cm silica gel, 8:2 hexane:ethyl acetate), affording 11.
$^1$H NMR (CDCl$_3$) δ10.09 (bs, 1H), 8.71 (dd, 1H, J=2.4 Hz), 8.66 (dd, 1H, J=2.4), 7.67 (d, 2H, J=7.9), 7.49 (d, 2H, J=8.8 Hz), 7.41 (t, 2H, J=7.7 Hz), 7.18 (t, 1H, J=7.3 Hz), 7.00 (d, 2H, J=8.6 Hz), 3.86 (s, 3H).

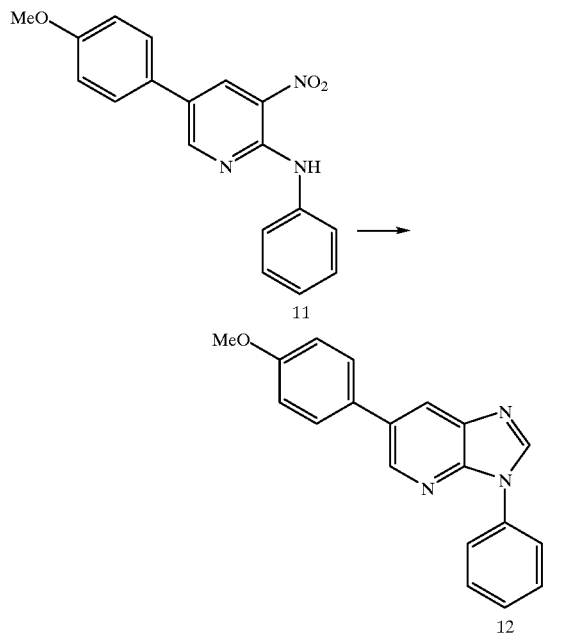

3-phenyl-6-(4-methoxylphenyl)imidazo[4,5-b]pyridine

Nitroaniline 11 (1.333 g, 4.15 mmol), Zn dust(6.239 g, 95.40 mmol), and 10 mL acetic acid were mixed under argon. The solution was heated to 60° C. for 1 hr until the solution turned light green. The zinc was removed using vacuum filtration with celite and washed with acetic acid. The filtrate was concentrated and 20 mL of trimethylorthoformate was added. The solution was heated to 100° C. for 2 hr followed by cooling to ambient temperature. The solution was concentrated and the crude mixture was purified by flash column chromatography(5×16 cm silica gel, 6:4 ethylacetate:hexane) affording 12.

$^1$H NMR (CDCl$_3$) δ8.61 (dd, 1H, J=2.0 Hz), 8.32 (s, 1H), 8.22 (dd, 1H, J=2.0), 7.74 (d, 2H, J=7.9 Hz), 7.55–7.50 (m, 4H), 7.39 (t, 1H, J=7.3), 6.99 (d, 2H, J=8.8 Hz), 3.80 (s, 3H). Mass spectrometry [M+H]$^+$302.3.

EXAMPLE 3

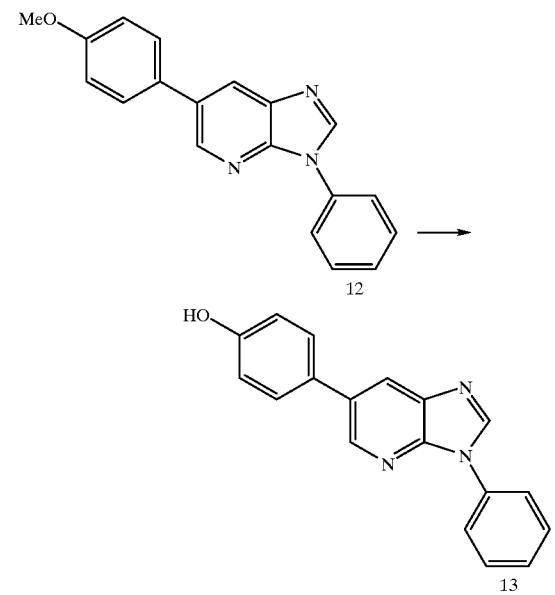

To the imidazopyridine 12 (202 mg, 0.670 mmol) was added a mixture of 10 mL hydrobromic acid and 10 mL acetic acid. The solution was stirred a room temperature for 5 min., followed by heating at 100° C. for 17 hr. The solution was cooled to ambient temperature and concentrated. Toluene (15 mL) was added and the solution was concentrated a second time. The concentrate was placed in vacuo over heating at 40° C. for 40 min., followed by further drying in vacuo at ambient temperature. Purification was acheived by reverse phase column chromatography affording 13.

$^1$H NMR (CD$_3$OD) δ9.45 (s, 1H), 8.82 (dd, 1H, J=1.8 Hz), 8.37 (dd, 1H, J=1.8 Hz), 7.91 (d, 2H, J=7.7 Hz), 7.68 (t, 2H, J=8.1Hz), 7.63–7.57 (m, 3H), 6.95 (d, 2H, J=8.6 Hz).

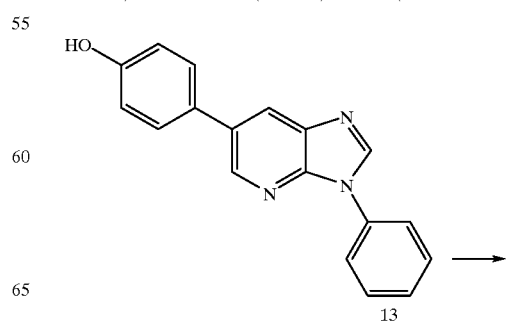

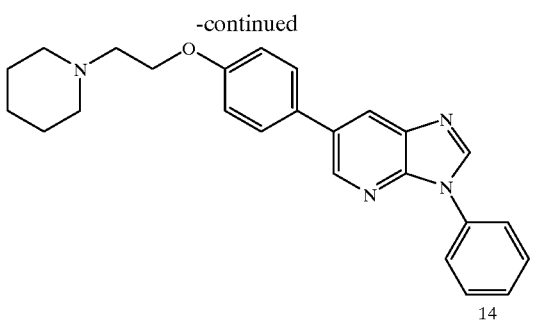

14

3-phenyl-6-(4-(2-(1-piperidinyl)ethoxy)phenyl)imidazo[4,5-b]pyridine

Cesium carbonate (296 mg, .908 mmol) and 1-(2-chloroethyl)piperidine monochlorohyrdide (84 mg, 0.454 mmol) were added under argon to a flame dried round bottom flask. Imidazopyridine 13 (87 mg, .303 mmol) was dissolved in 1.5 mL of anhydrous N,N dimethyl formamide under argon. The vessel was heated at 50° C. for 16 hr. and cooled to ambient temperature. The solution was diluted to 100 mL with saturated sodium bicarbonate, and the product was extracted using ethyl acetate. The aqueous layer was extracted a second time with dichloromethane w/3% 1-butanol. The organic layers were washed with saturated sodium bicarbonate, and dried over sodium sulfate. The organic layers were concentrated at aspirator pressure to remove ethyl acetate and methylene chloride; the 1-butanol and residual DMF were removed under high pressure. The product was purified using flash column chromatography (silica gel 2.5×32.5 cm, 10:1 methylene chloride:methanol). Excess trifluoroacetic acid was added to the product to create the resulting salt, and the mixture was triturated using ether. The TFA salt was dried using phosphorous pentoxide in vacuo to yield 14 (1.10 TFA salt).

$^1$H NMR (CD$_3$OD) $\delta$8.66 (s, 1H), 8.55 (dd, 1H, J=2.0 Hz), 8.17 (dd, 1H, J=2.0 Hz), 7.82 (d, 2H, J=8.6 Hz), 7.59–7.52 (m, 4H), 7.46 (t, 1H, J=7.5 Hz), 7.01 (d, 2H, J=8.8 Hz), 4.85 (s, 2H), 4.15 (t, 2H, J=5.5 Hz), 2.84 (t, 2H, J=5.5 Hz), 2.62 (bs, 4H), 1.65 (m, 4H), 1.50 (m, 2H). Anal. Calcd. for C$_{25}$H$_{26}$N$_4$O.1.10 TFA: C, 62.35; H, 5.21; N, 10.69. Found: C, 62.32; H, 4.93; N, 10.53.

EXAMPLE 4

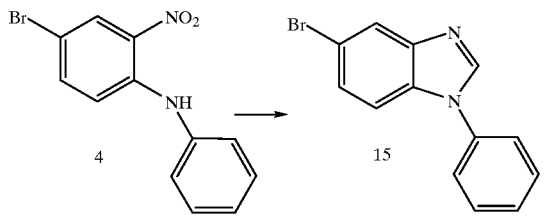

Bromoaromatic 4 (7.10 g, 24.1 mmol) and powder ed zinc (3 6.2 g, 554 mmol, 23 equiv) were stirred in 80 mL glacial acetic acid. The mixture was heated to 60° C. After 1 h the reaction was cooled and filtered through a plug of celite and concentrated to dryness. The resulting residue was dissolved in 60 mL of formic acid and heated to 100° C. overnight. The reaction was cooled and concentrated to dryness. Purification by flash column chromatography (6×25 cm silica, 55:45 hexanes/EtOAc) afforded 5.88 g benzimidazole 15 (89% yield). $^1$H NMR(CDCl$_3$) $\delta$8.18 (s, 1H), 8.05 (d, 1H, J=1.7 Hz), 7.60 (t, 2H, J=7.1 Hz), 7.54–7.48 (m, 3H), 7.46 (dd, AH, J=1.8, 8.8 Hz), 7.40 (d, 1H, J=8.8 Hz).

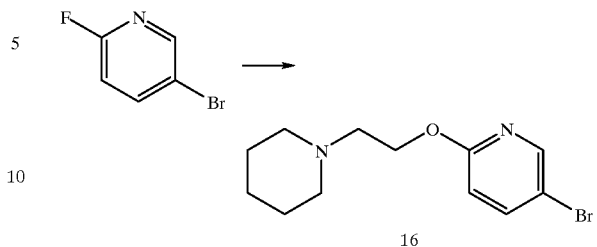

1-Piperidineerthanol (1.13 mL, 8.51 mmol) was dissolved in 10 mL anhydrous DMF under Ar. The solution was cooled to 0° C. and NaH (225 mg, 9.38 mmol) was added. After 10 min the mixture was allowed to warm to room temperature and 5-bromo-2-fluoropyridine (1.50 g, 8.52 mmol) was added. After 1h the reaction was quenched with water and extracted 3x with EtOAc. The combined extracts were dried over Na2SO4, filtered and concentrated to afford 2.20 g (91% yield) of the alkoxypyridine 16. $^1$H NMR(CDCl$_3$) $\delta$8.17 (d, 1H, J=2.6 Hz), 7.62 (dd, 1H, J=2.6, 8.8 Hz), 6.67 (d, 1H, J=8.8 Hz), 4.40 (t, 2H, J=6.0 Hz), 2.74 (t, 2H, J=5.9 Hz), 2.49 (m, 4H), 1.60 (m, 4H), 1.44 (m, 2H).

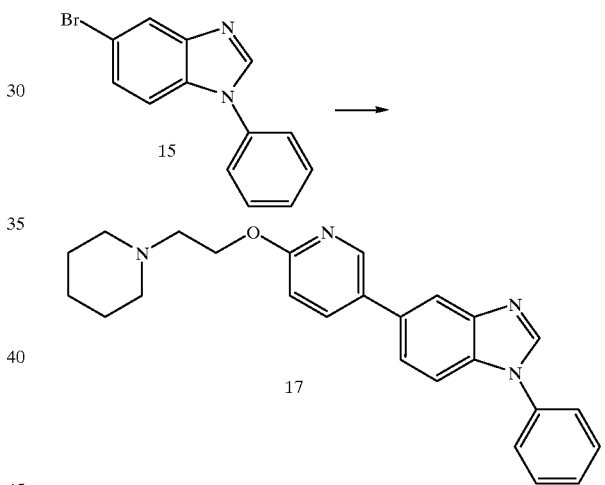

1-Phenyl-5-[6-(2-piperidin-1-yl-ethoxy)-pyridin-3-yl]-1H-benzimidazole

Benzimidazole 15 (2.91 g, 10.7 mmol), diboron pinacol ester (2.97 g, 11.7 mmol) and potassium acetate (3.14 g, 32.0 mmol) were stirred in 20 mL anhydrous DMF under Ar. PdCl$_2$(dppf) (0.26 g, 0.32 mmol) was added, solution was degassed and heated to 80° C. After 20 h the reaction was quenched with 125 mL of water and 50 mL of saturated aqueous NaCl and was extracted 3 x with EtOAc. The combined extracts were dried over Na$_2$SO$_4$, filtered and concentrated to afford 2.77 g of unpurified boronate. The unpurified boronate (650 mg, 2.03 mmol), alkoxypyridine 16 (526 mg, 1.85 mmol), 2M Na$_2$CO$_3$ (861 mg, 8.12 mmol), and 4 mL dioxane were added to a round bottom flask. After flushing three times with argon, Pd(PPh$_3$)$_4$ (117 mg, 10 mmol) was added, and the vessel was again flushed three times with argon. The vessel was heated to 80° C. under argon. After 22 hr., the reaction was cooled to room temperature followed by quenching with 25 mL water. The mixture was extracted with 4×20 mL ethyl acetate, and the combined organic layers were washed with 1×20 mL brine. The organic layer was dried over sodium sulfate, filtered, and concentrated. Purification was performed using reverse phase column chromatography (Waters 2×40 mm C-18 column, H₂O: acetonitrile mobile phase gradient). The resulting oil was triturated with ether, filtered and washed with ether, affording 16, a white TFA salt(150 mg, 16% yield). Mp: 160.5–162° C. ¹H NMR(CDCl₃) δ8.41 (d, 1H, J=2.4 Hz), 8.19 (s, 1H), 8.01 (d, 1H, J=1.3 Hz), 7.90 (dd, 1H, J=11.0 Hz), 7.61 (m, 3H, J=13.6), 7.52 (m, 4H, J=31.0 Hz), 6.86 (d, 1H, J=8.4 Hz), 4.79 (t, 2H, J=9.9 Hz), 3.76 (bd, 2H, J=11.9 Hz), 3.51 (t, 2H, J=9.7 Hz), 2.80 (bt, 2H, J=23.1Hz), 2.06 (m, 2H, J=26.2 Hz), 1.89 (s, 2H), 1.65 (s, 2H).

EXAMPLE 5

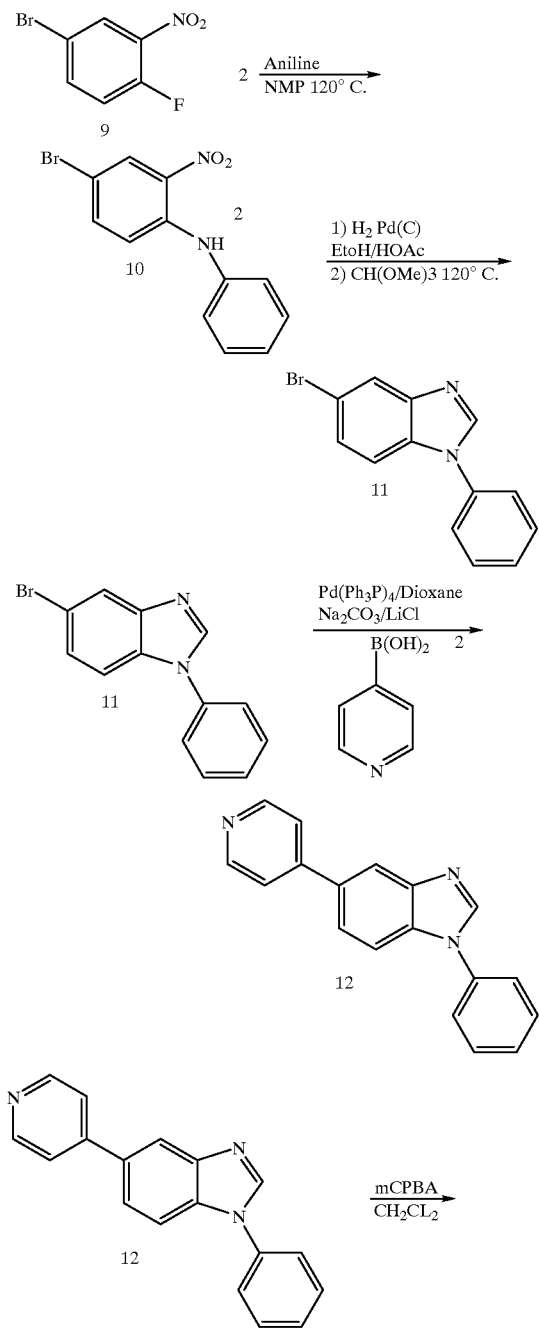

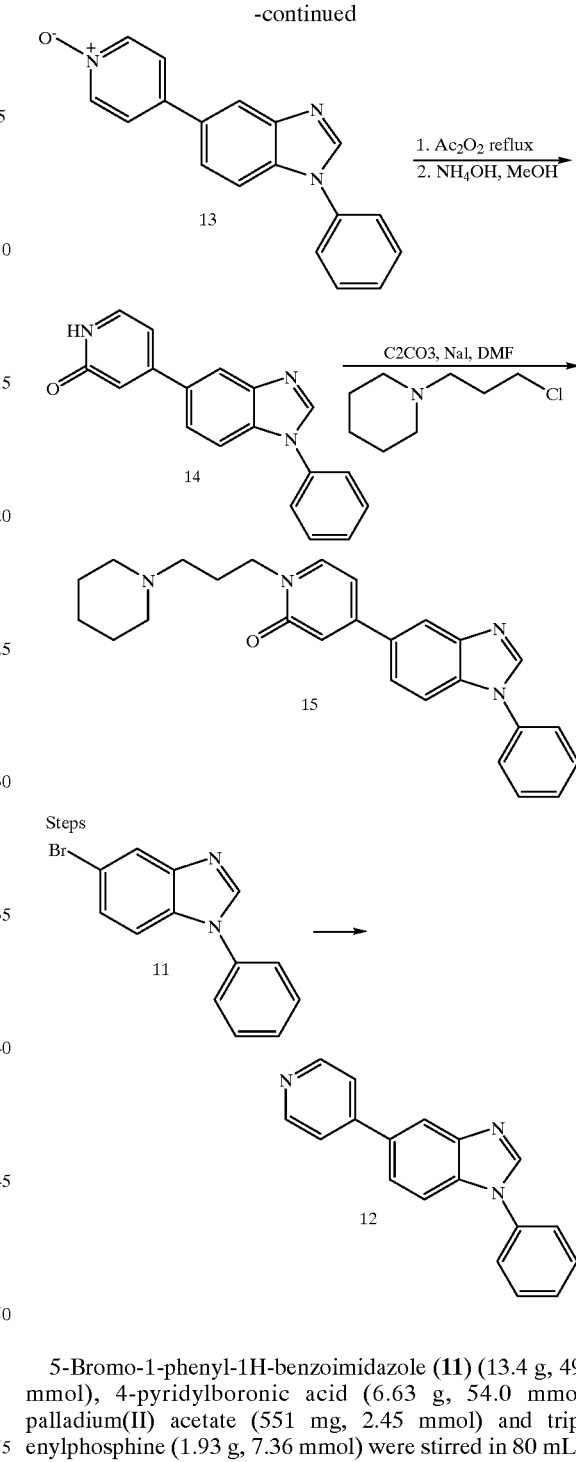

5-Bromo-1-phenyl-1H-benzoimidazole (11) (13.4 g, 49.1 mmol), 4-pyridylboronic acid (6.63 g, 54.0 mmol), palladium(II) acetate (551 mg, 2.45 mmol) and triphenylphosphine (1.93 g, 7.36 mmol) were stirred in 80 mL of n-PrOH in a flask equipped with a reflux condenser, under Ar. Sodium carbonate (6.24 g, 58.9 mmol) was dissolved in 30 mL of water and the resulting solution was added to the nPrOH mixture. The resulting mixture was degassed three times by alternating vacuum and argon atmoshphere. The reaction was then heated to reflux. After 18 h the reaction as cooled, diluted with water and extracted three times with EtOAc. The combined extracts were washed with sat. NaCl (aq), dried over sodium sulfate, filtered and concentrated. Purification by flash column chromatography (95:5 CH₂Cl₂/MeOH) afforded 8.82 g of 1-phenyl-5-pyridin-4-yl-1H-benzoimidazole (66% yield). 1H NMR (CDCl3) δ8.68 (d, J=6.0 Hz, 2H), 8.18 (s, 1H), 8.17 (s, 1H), 7.63–7.59 (m, 6H), 7.56–7.51 (m, 3H). Mass Spectrometry (for C18H13N3): [M+H]+272.1182, theoretical 272.1182.

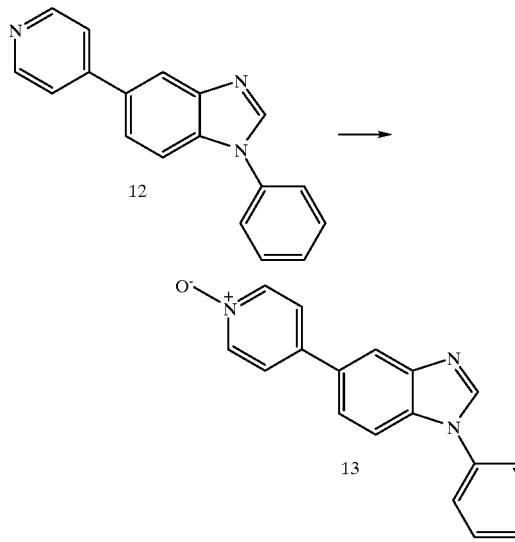

1-Phenyl-5-pyridin-4-yl-1H-benzoimidazole (12) (8.82 g, 32.5 mmol) was dissolved in 120 mL of $CH_2Cl_2$. The resulting solution was cooled to 0° C. and to it was added mCPBA (11.2 g, 65.0 mmol). After stirring for 2.5 days an additional portion of mCPBA (3.0 g, 17 mmol) was added. After an additional 24 h the reaction solution was loaded directly onto a column (8×20 cm) pre-wetted with $CH_2Cl_2$. The resulting flash column chromatography, eluting with 9:1 $CH_2Cl_2$/MeOH, afforded 7.40 g of 5-(1-oxy-pyridin-4-yl)-1-phenyl-1H-benzoimidazole (13) (79% yield). $^1$H NMR (CDCl$_3$) δ 8.40 (d, J=6.0 Hz, 2H), 8.18 (s, 1H), 8.11 (d, J=1.5 Hz, 1H), 7.66–7.47 (m, 9H). Mass Spectrometry (for $C_{18}H_{13}N_3$): [M+H]+288.1131, theoretical 288.1131.

5-(1-Oxy-pyridin-4-yl)-1-phenyl-1H-benzoimidazole (13)

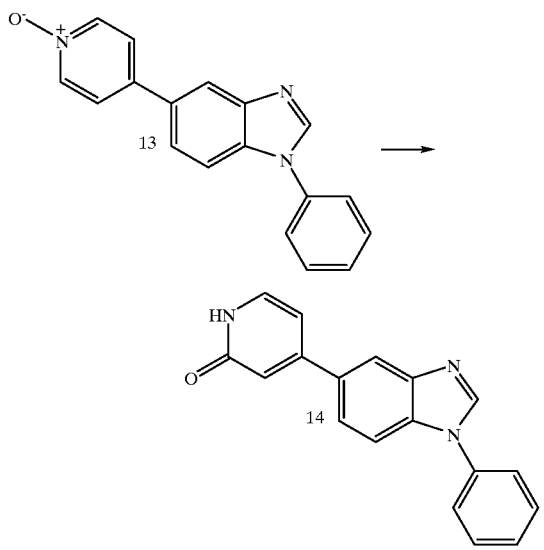

(7.40 g, 25.8 mmol) was stirred in 48.6 mL of acetic anhydride (52.6 g, 515 mmol) and the resulting mixture was heated to reflux. After 8 h the reaction was concentrate to dryness and the resulting residue was dissolved in 50 mL MeOH. Concentrated ammonium hydroxide (10 mL) was added and the solution was stirred for 16 h. The solution was then concentrated to dryness and the residue was purified by flash column chromatography (elute with 95:5–90:10 $CH_2Cl_2$/MeOH) to afford 4.57 g of 4-(1-phenyl-1H-benzoimidazol-5-yl)-1H-pyridin-2-one (14) (62% yield). $^1$H NMR (CDCl$_3$) δ11.59 (bs, 1H), 8.18 (s, 1H), 8.13 (d, J=0.9 Hz, 1H), 7.64–7.60 (m, 4H), 7.55–7.51 (m, 3H), 7.42 (d, J=7.0 Hz, 1H), 6.88 (d, J=1.3 Hz, 1H), 6.65 (dd, J=1.8, 7.0 Hz, 1H). Elemental analysis (for 0.40 hydrate): Calc'd C, 73.40, H, 4.72, N, 14.27; Found C, 73.33, H, 5.00, N. 13.91.

4-(1-phenyl-1H-benzoimidazol-5-yl)-1H-pyridin-2-one (14)

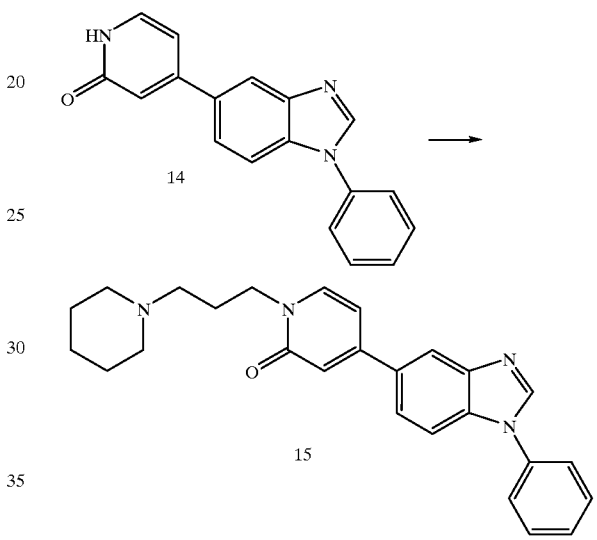

(4.57 g, 15.9 mmol) was dissolved in 30 mL anhydrous DMF under Ar. Sodium iodide (2.86 g, 19.1 mmol), cesium carbonate (11.9 g, 36.6 mmol) and N-chloropropylpiperidine HCl salt (3.78 g, 19.1 mmol) were added and the reaction was warmed to 40° C. After 3 days additional portions of N-chloropropylpiperidine HCl salt (1.9 g, 9.6 mmol) and cesium carbonate (6.0 g, 18 mmol) were added. After an addtional 16 h the bulk of the DMF was removed in vacuo. The residue was diluted with water and extracted 3x with 5% n-BuOH in $CH_2Cl_2$. The combined organic phases was dried over $Na_2SO_4$, filtered and concentrated. The residue was purified in several batches by preperative reverse phase HPLC, dissolving sample in MeOH, eluting with 5:95 acetonitrile/water (0.1% H3PO4) to 50:50. Fractions containing pure product were concentrated to remove the bulk of the acetonitrile, basified to pH 8 w/$Na_2CO_3$ (s), and extraced 3x with 5% BuOH in $CH_2Cl_2$. The combined organic phases were dried over $Na_2SO_4$, filtered and concentrated to afford 3.70 g of pure 4-(1-phenyl-1H-benzoimidazol-5-yl)-1-(3-piperidin-1-yl-propyl)-1H-pyridin-2-one (15). $^1$H NMR (CDCl$_3$) δ8.17 (s, 1H), 8.10 (s, 1H), 7.63–7.50 (m, 7H), 7.45 (d, J=7.1Hz, 11H), 6.85 (d, J=1.6 Hz, 1H), 6.52 (dd, J=1.8, 7.1Hz, 1H), 4.05 (t, J=6.8 Hz, 2H), 2.38–2.34 (m, 4H), 2.00 (t, J=6.8 Hz, 2H), 1.65–1.58 (m, 6H), 1.45 (M, 2H). Elemental analysis: Calc'd C, 75.70, H, 6.84, N, 13.58; Found C, 75.32, H. 6.87, N. 13.37.

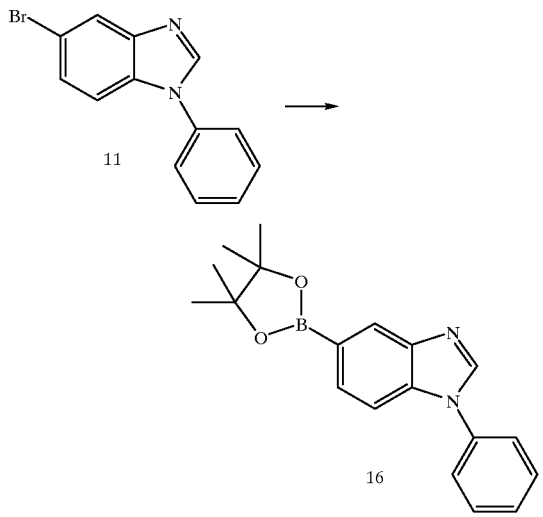

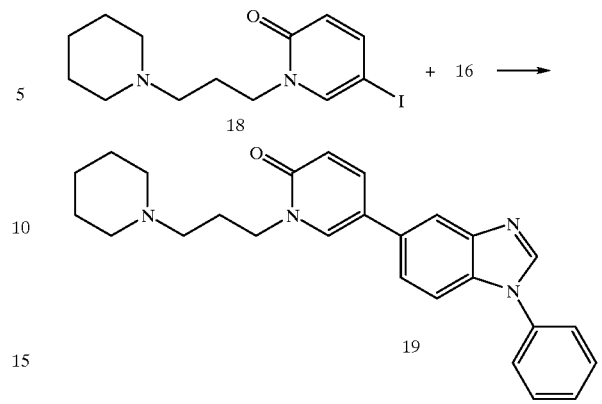

5-Bromo-1-phenyl-1H-benzoimidazole (11) (9.71 g, 35.6 mmol), diboron pinacol ester (9.93 g, 39.1 mmol), potassium acetate (10.5 g, 107 mmol) and dichloro[1,1'-bis (diphenylphosphino)ferrocene]palladium(II) dichloromethane adduct (0.78 g, 1.1 mmol) were stirred in 40 mL anhydrous DMF under Ar. The solution was degassed three times by alternating vacuum and argon atmosphere. The reaction was heated to 80° C. for 1 8 h. After cooling the reaction was diluted with water and extracted 3x with EtOAc. The combined organic phases were dried over $Na_2SO_4$, filtered and concentrated to afford 11.8 g 1-phenyl-5-(4,4,5,5-tetramethyl-[1,3,2]dioxaborolan-2-yl)-1H-benzoimidazole (16) which was used without purification.

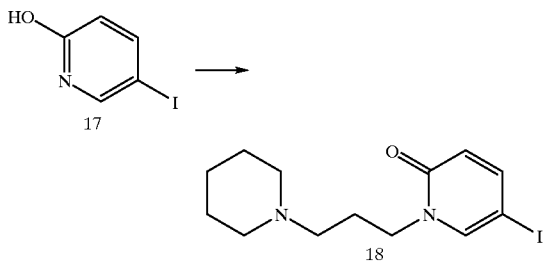

Sodium hydride (0.073 g, 3.0 mmol) was stirred in 4 mL anhydrous DMF under Ar. The solution was cooled to 0° C. and 3-iodo-5-hydroxypyridine (0.305 g, 1.38 mmol) was added gradually. After bubbling had subsided N-chloropropylpiperidine hydrochloride (0.330 g, 1.67 mmol) was added slowly. The reaction was then allowed to warm to ambient temperature. After 40 h the reaction was diluted with water and extracted 3x with EtOAc. The combined organic phases were washed was washed with saturated NaCl (aq), dried over $Na_2SO_4$, filtered and concentrated. Purification by flash column chromatography (2×16 cm silica, 9:1 CH2Cl2/MeOH) afforded 192 mg 5-iodo-1-(3-piperidin-1-yl-propyl)-1H-pyridin-2-one (18) (40% yield). $^1$H NMR (CDCl$_3$) δ7.72 (d, J=2.6 Hz, 1H), 7.40 (dd, J=2.6, 9.5 Hz, 1H), 6.37 (d, J=9.5 Hz, 1H), 3.96 (t, J=6.6 Hz, 2H), 2.35 (bs, 4H), 2.26 (t, J=6.6 Hz, 2H), 1.92 (t, 6.6 Hz, 2H), 1.60 (m, 4H), 1.46 (m, 2H).

5-iodo-1-(3-piperidin-1-yl-propyl)-1H-pyridin-2-one (18) (0.096 g, 0.28 mmol), 1-phenyl-5-(4,4,5,5-tetramethyl-[1,3,2]dioxaborolan-2-yl)-1H-benzoimidazole (0.081 g, 0.25 mmol), palladium(II) acetate (0.003 g, 0.013 mmol), triphenylphosphine (0.010 g, 0.038 mmol) and sodium carbonate (0,080 g, 0.75 mmol) were stirred in 1.6 mL of a 3:1 mixture of dioxane/water. The mixture was degassed 3x by alternating vacuum and an argon atmosphere. The reaction was heated to 80° C. for 18 h, cooled and diluted with water. The aqueous phase was extracted 3x with EtOAc and the resulting organic phase was dried over $Na_2SO_4$, filtered and concentrated. Purification by flash column chromatography (eluted with 85:15 $CH_2Cl_2$/MeOH) afforded 0.073 g 5-(1-phenyl-1H-benzoimidazol-5-yl)-1-(3-piperidin-1-yl-propyl)-1H-pyridin-2-one (19) (71% yield). $^1$H NMR (CDCl$_3$) o 9.60 (s, 1H), 7.90 (d, J=1.3 Hz, 1H), 7.74–7.67 (m, 2H), 7.64–7.48 (m, 6H), 7.39 (dd, J=2.5, 9.5 Hz, 1H), 6.68 (d, J=9.5 Hz, 1H), 4.13 (t, J=6.5 Hz, 2H), 2.42 (bs, 6H), 2.10 (t, J=6.5 Hz, 2H), 1.64 (m, 4H), 1.46 (m, 2H). Mass Spectrometry (for $C_{26}H_{28}N_4O$): [M+H]+413.2334, theoretical 413.2336.

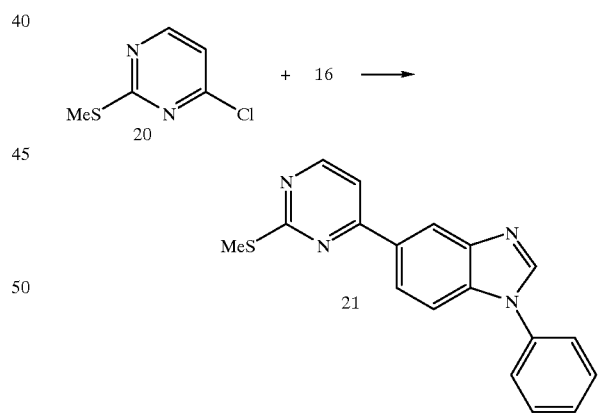

To a flame dried round bottom flask with stir bar was added 1-phenyl-5-(4,4,5,5-tetramethyl-[1,3,2]dioxaborolan-2-yl)-1H-benzoimidazole (16) (2.00 g, 6.25 mmol), triphenylphosphine (147 mg, .562 mmol) palladium(II) acetate (42 mg, 0.187 mmol), 2M aqueous $Na_2CO_3$ (9.37 mL, 18.7 mmol), 4-chloro-2-methylthiopyrimidine (1.00 g, 6.24 mmol), 3 mL water, and 14 InL of 1-propanol. Vessel was flushed three times with argon and placed in 80° C. oil bath with stirring. Reaction was complete after 1.7 hr by HPLC—cooled to RT and removed solvent under vacuum. Workup included dissolution into 150 mL ethyl acetate, adding 50 mL 1/2 saturated aqueous NaHCO₃, extracting, then extracting the aqueous layer again with 2×40 mL EtOAc. Washed combined organics with 1×50 mL ½ saturated brine, dried over Na₂SO₄, filtered, and concentrated under vacuum. Performed purification via flash column chromatography (60 mm×200 mm silica gel, 20:1 CH₂Cl₂:MeOH mobile phase) to afford 1.54 g of compound (21) (77% yield). ¹HNMR(CDCl₃) δ8.64 (d, 1H), 8.56 (d, 1H) 8.20 (s, 1H), 8.18 (dd, 1H), 7.63 (m, 3H), 7.53 (m, 3H), 7.47 (d, 1H), 2.68 (s, 3H).

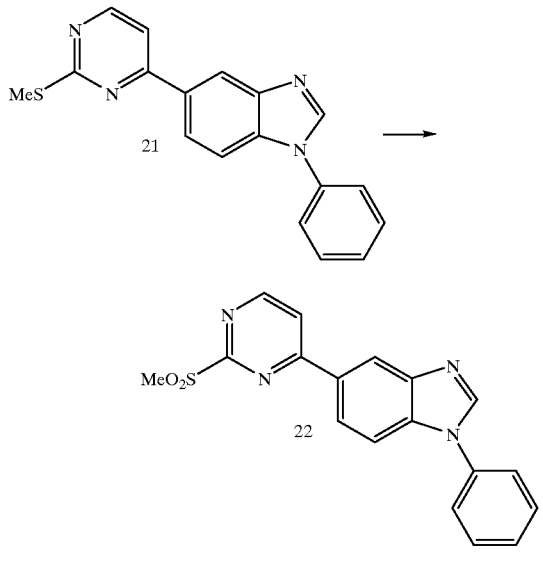

To a stirred suspension of Oxone (potassium peroxymonosulfate, 11.87 g, 19.31 mmol) in water at 0° C. was added a suspension of the starting methyl sulfide benzimidazole (21) (1.54 g, 4.83 mmol) in MeOH. The reaction mixture was allowed to warm to RT and was monitored by HPLC. The starting methyl sulfide changed from the methyl sulfoxide to the methyl sulfone over the course of 12 hr. The MeOH was removed under vacuum after the reaction was complete. The reaction mixture was extracted with 3×40 mL CH₂Cl₂. The combined organic layers were washed with 40 mL brine, dried over Na₂SO₄, filtered, and the solvent removed under vacuum to afford 1.5 g (22) (90% crude yield). ¹HNMR: (CDCl₃) δ 8.92 (d, 1H, J=5.3 Hz), 8.66 (d, 1H, J=1.6 Hz), 8.27 (dd, 1H, J=1.6, 7.1Hz), 8.23 (s, 1H), 8.00 (d, 1H, J=5.4 Hz), 7.65 (m, 3H), 7.54 (m, 3H), 3.47 (s, 3H).

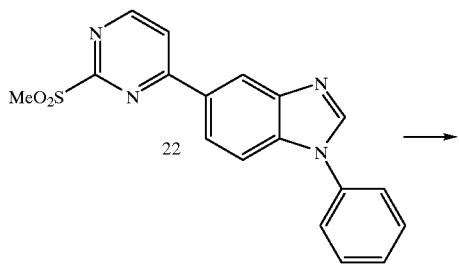

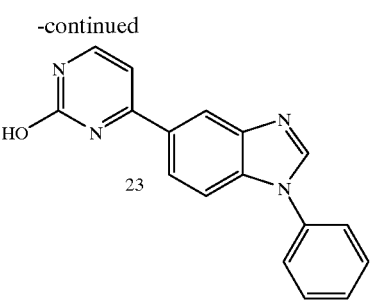

To a flask containing the starting methyl sulfone (500 mg, 1.427 mmol) was added 56% LIOH hydrate (244 mg, 5.708 mmol). To this vessel was added 5 mL tetrahydrofuran and 5 mL water. The reaction mixture was cooled to 0° C. for 2 hr, then gradually was allowed to warm to RT. The reaction was stirred at RT overnight. The reaction was complete after 20 hr and the THF via low vacuum rotary evaporation and water by high vacuum rotary evaporation. The crude material was diluted in 15 mL MeOH, sonicated, and filtered through cotton and a 0.7 μM syringe filter into round bottom flask. The filtrate was concentrated to afford 480 mg of unpurified product (23). The solvent was again removed via rotary evaporation. ¹H NMR: (CD₃OD) δ8.47 (s, 1H), 8.40 (s, 1H), 8.20 (d, 1H, J=5.2 Hz), 8.07 (dd, 1H, J=1.4, 7.3 Hz), 7.65 (m, 5H), 7.55 (m, 1H), 6.92 (d, 1H, J=5.3 Hz). High resolution mass spectometry: Measured mass=289.1068 (289.1084 theoretical mass).

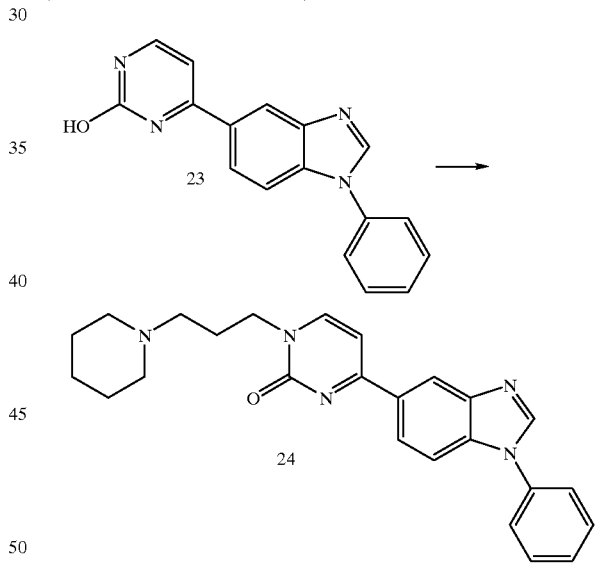

To a flask containing the starting benzimidazole (23) (66 mg, 0.229 mmol) was added N-3-chloropiperidine HCl (54 mg, .275 mmol), cesium carbonate (164 mg, 0.504 mmol) and 4 mL anhydrous N,N-dimethylformamide. The vessel was placed in 60° C. oil bath with stirring under argon. The reaction was heated to 80° C. after 1 day, and was stopped after 4 days after no further progression. The solvent was removed via high vacuum rotary evaporation, the residue was diluted with MeOH, and filtered through a 0.7 μM syringe filter. Reverse phase column chromatography (Waters 2×40 mm C-18 stationary phase, ACN:H₂O mobile phase gradientcontaining 1% TFA). Concentrated appropriate HPLC fractions to afford two distinct products— confirmed to be N-alkylated and O-alkylated isomers by mass spectrometry (low res. M+1=414.3 ) and ¹H NMR.

Yields of the TFA salts were: N-alkylated (24) (38.6 mg, 32% yield), O-alkylated (not shown) (6.2 mg, 5% yield). The ¹HNMR for 4-(1-phenyl-1H-benzoimidazol-5-yl)-1-(3-piperidin-1-yl-propyl)-1H-pyrimidin-2-one is as follows: (CDCl₃) δ8.63 (d, 1H, J=7.9 Hz), 8.34 (d, 1H, J=10.1Hz), 7.92 (d, 1H, J=6.9 Hz), 7.62 (m, 6H), 7.01 (d, 1H, J=7.0 Hz), 4.11 (t, 2H, J=7.0 Hz), 3.64 (m, 2H), 3.17 (m, 2H), 2.68 (m, 2H), 2.39 (m, 2H), 1.92 (m, 6H).

The following compounds can be made by literature methods and/or in combination with methods disclosed herein.

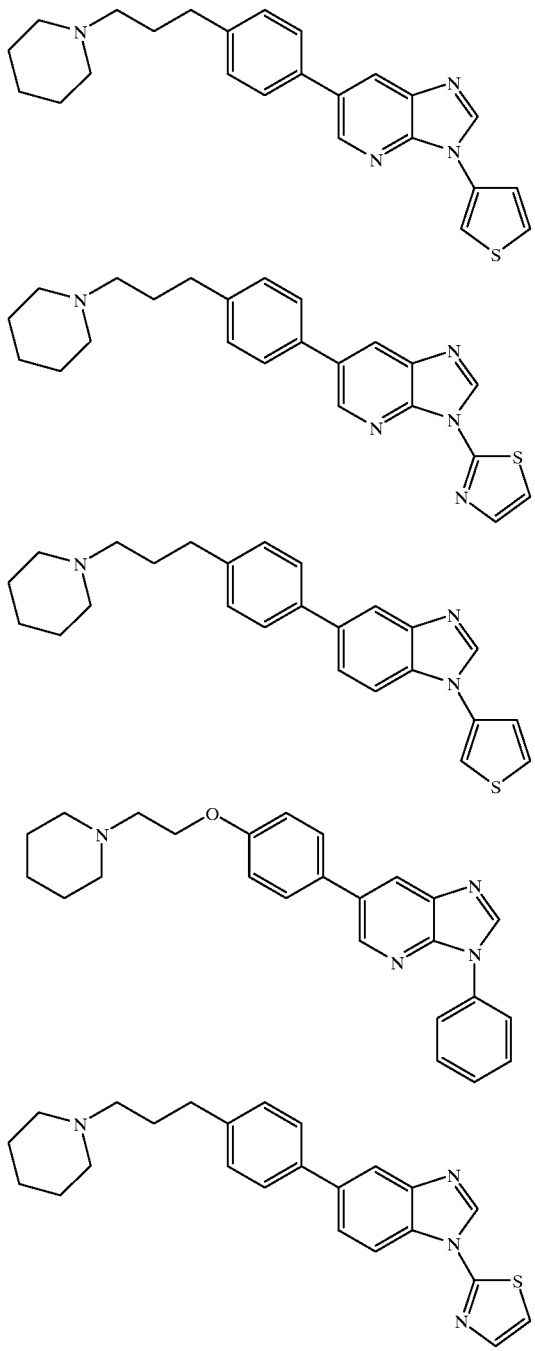

Kinase inhibition is demonstrated in accordance with the following protocol.

VEGF RECEPTOR KINASE ASSAY

VEGF receptor kinase activity is measured by incorporation of radio-labeled phosphate into polyglutamic acid, tyrosine, 4:1 (pEY) substrate. The phosphorylated pEY product is trapped onto a filter membrane and the incoporation of radio-labeled phosphate quantified by scintillation counting.

MATERIALS

VEGF Receptor Kinase

The intracellular tyrosine kinase domains of human KDR (Terman, B. I. et al. Oncogene (1991) vol. 6, pp. 1677–1683.) and Flt-1(Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

Lysis Buffer 50 mM Tris pH 7.4, 0.5 M NaCl, 5 mM DTT, 1 mM EDTA, 0.5% triton X-100, 10 % glycerol, 10 mg/ml of each leupeptin, pepstatin and aprotinin and lmM phenylmethylsulfonyl fluoride (all Sigma).

Wash Buffer 50 mM Tris pH 7.4, 0.5 M NaCl, 5 mM DTT, 1 mM EDTA, 0.05% triton X-100, 10 % glycerol, 10 mg/ml of each leupeptin, pepstatin and aprotinin and 1 mM phenylmethylsulfonyl fluoride.

Dialysis Buffer 50 mM Tris pH 7.4, 0.5 M NaCl, 5 mM DTT, 1 mM EDTA, 0.05% triton X-100, 50 % glycerol, 10 mg/ml of each leupeptin, pepstatin and aprotinin and ImM phenylmethylsuflonyl fluoride

10 X Reaction Buffer 200 mM Tris, pH 7.4, 1.0 M NaCl, 50 mM MnCl₂, 10 mM DTT and 5 mg/ml bovine serum albumin (Sigma).

Enzyme Dilution Buffer 50 mM Tris, pH 7.4, 0.1 M NaCl, 1 mM DTT, 10 % glycerol, 100 mg/ml BSA.

10 X Substrate

750 μg/ml poly (glutamic acid, tyrosine; 4:1) (Sigma).

Stop Solution

30% trichloroacetic acid, 0.2 M sodium pyrophosphate (both Fisher).

Wash Solution

15% trichloroacetic acid, 0.2 M sodium pyrophosphate.

Filter Plates

Millipore #MAFC NOB, GF/C glass fiber 96 well plate.

METHOD

A. Protein Purification

1. Sf21 cells were infected with recombinant virus at a multiplicity of infection of 5 virus particles/ cell and grown at 27° C. for 48 hours.

2. All steps were performed at 4° C. Infected cells were harvested by centrifugation at 1000 X g and lysed at 4° C. for 30 minutes with 1/10 volume of lysis buffer followed by centrifugation at 100,000Xg for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 $\mu$l of inhibitor or control to the assay in 50% DMSO.
2. Add 35 $\mu$l of reaction mix containing 5 $\mu$l of 10 X reaction buffer, 5 $\mu$l 25 mM ATP/10 $\mu$Ci [$^{33}$P]ATP (Amersham), and 5 $\mu$l 10 X substrate.
3. Start the reaction by the addition of 10 $\mu$l of KDR (25 nM) in enzyme dilution buffer.
4. Mix and incubate at room temperature for 15 minutes.
5. Stop by the addition of 50 $\mu$l stop solution.
6. Incubate for 15 minutes at 4° C.
7. Transfer a 90 $\mu$l aliquot to filter plate.
8. Aspirate and wash 3 times with wash solution.
9. Add 30 $\mu$l of scintillation cocktail, seal plate and count in a Wallac Microbeta scintillation counter.

Human Umbilical Vein Endothelial Cell Mitogenesis Assay

Expression of VEGF receptors that mediate mitogenic responses to the growth factor is largely restricted to vascular endothelial cells. Human umbilical vein endothelial cells (HWECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HWECs

HUVECs frozen as primary culture isolates are obtained from Clonetics Corp. Cells are maintained in Endothelial Growth Medium (EGM; Clonetics) and are used for mitogenic assays at passages 3–7.

Culture Plates

NUNCLON 96-well polystyrene tissue culture plates (NUNC #167008).

Assay Medium

Dulbecco's modification of Eagle's medium containing 1 g/ml glucose (low-glucose DMEM; Mediatech) plus 10% (v/v) fetal bovine serum (Clonetics).

Test Compounds

Working stocks of test compounds are diluted serially in 100% dimethylsulfoxide (DMSO) to 400-fold greater than their desired final concentrations. Final dilutions to 1X concentration are made directly into Assay Medium immediately prior to addition to cells.

10X Growth Factors

Solutions of human VEGF$_{165}$ (500 ng/ml; R&D Systems) and bFGF (10 ng/ml; R&D Systems) are prepared in Assay Medium.

10X [$^3$]Thymidine

[Methyl-$^3$H]Thymidine (20 Ci/nmiol; Dupont-NEN) is diluted to 80 $\mu$Ci/ml in low-glucose DMEM.

Cell Wash Medium

Hank's balanced salt solution (Mediatech) containing 1 mg/ml bovine serum albumin (Boehringer-Mannheim).

Cell Lysis Solution

1 N NaOH, 2% (w/v) Na$_2$CO$_3$.

Method

1. HUVEC monolayers maintained in EGM are harvested by trypsinization and plated at a density of 4000 cells per 100 ul Assay Medium per well in 96-well plates. Cells are growth-arrested for 24 hours at 37° C. in a humidified atmosphere containing 5% CO$_2$.
2. Growth-arrest medium is replaced by 100 ul Assay Medium containing either vehicle (0.25% [v/v] DMSO) or the desired final concentration of test compound. All determinations are performed in triplicate. Cells are then incubated at 37° C./5% CO$_2$ for 2 hours to allow test compounds to enter cells.
3. After the 2-hour pretreatment period, cells are stimulated by addition of 10 $\mu$l/well of either Assay Medium, lOX VEGF solution or 10X bFGF solution. Cells are then incubated at 37° C./5% CO$_2$.
4. After 24 hours in the presence of growth factors, 10X [$^3$H]Thymidine (10 ul/well) is added.
5. Three days after addition of [$^3$H]thymidine, medium is removed by aspiration, and cells are washed twice with Cell Wash Medium (400 ul/well followed by 200 ul/well). The washed, adherent cells are then solubilized by addition of Cell Lysis Solution (100 ul/well) and warming to 37° C. for 30 minutes. Cell lysates are transferred to 7-ml glass scintillation vials containing 150 ul of water. Scintillation cocktail (5 ml/vial) is added, and cell-associated radioactivity is determined by liquid scintillation spectroscopy.

Based upon the foregoing assays the compounds of formula I are inhibitors of VEGF and thus are useful for the inhibition of neoangiogenesis, such as in the treatment of occular disease, e.g., diabetic retinopathy and in the treatment of cancers, e.g., solid tumors. The instant compounds inhibit VEGF-stimulated mitogenesis of human vascular endothelial cells in culture with IC$_{50}$ values between 150–650 nM. These compounds also show selectivity over related tyrosine kinases (e.g. FGFR1 and the Src family).

What is claimed is:

1. A compound of the structural formula

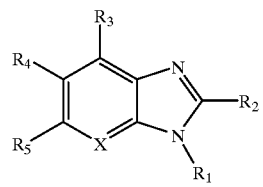

I or a pharmaceutically acceptable salt, hydrate or prodrug thereof,

X is C—H;

$R_1$ is phenyl, thienyl, or thiazolyl, said phenyl, thienyl and thiazolyl is optionally substituted with one to three members selected from $R^a$;

$R_2$ and $R_3$ are independently selected from H, $C_{1-6}$ alkyl, aryl, $C_{3-6}$ cycloalkyl, OH, $NO_2$, $NH_2$, and halo;

$R_4$ is selected from the group consisting of:
phenyl, pyridinyl, pyridinyl N-oxide, pyridinone, pyrimidinyl, and pyrimidinone, optionally substituted with one to three members selected from $R^a$, with the proviso that $R_4$ is not phenyl if $R_1$ is phenyl and that $R_4$ be substituted with OR or $NR_7R_8$ if $R_4$ is pyridl when $R_1$ is phenyl;

$R_5$ is H, $C_{1-6}$ alkyl, OR, halo, $NH_2$ or $NO_2$;

$R^a$ is $C_{1-10}$ alkyl, halogen, $NO_2$, OR, $NR_7R_8$, aryl, or $C_{3-10}$ heterocyclyl;

R is: $C_{1-6}$ alkyl, optionally substituted with aryl or heterocyclyl, said aryl and heterocyclyl are optionally substituted with $C_{1-10}$ alkyl, halogen, $NO_2$, $OC_{1-6}$ alkyl, CN, $NR_7R_8$, aryl, or heterocyclyl; and $R_7$ and $R_8$ are independently selected from the group consisting of:
H, $C_{1-10}$ alkyl, $C_{3-6}$ cycloalkyl, $COC_{1-6}$ alkyl, aryl, and $C_{3-10}$ heterocyclyl,
or $NR_7R_8$ can be taken together to form piperidinyl, pyrryl, pyrrolidyl, imidazolyl, or piperzinyl.

2. A compound in accordance with claim 1 wherein:

$R_2$ and $R_3$ are independently selected from H, $C_{1-6}$ alkyl, $C_{3-6}$cycloalkyl, OH, and halogen.

3. A compound in accordance with claim 1 wherein:

$R_2$ and $R_3$ are independently H or $C_{1-6}$ alkyl.

4. A compound of the structural formula IIa

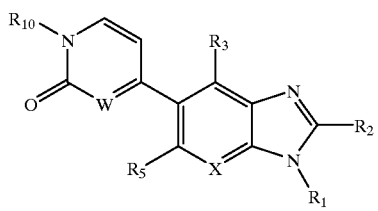

IIa or a pharmaceutically acceptable salt, hydrate or prodrug thereof,
wherein

X is C—H;

W is N or C—H;

$R_1$ and $R_3$ are independently selected from the group consisting of:
H, $C_{1-10}$ alkyl, $C_{3-6}$ cycloalkyl, aryl, halo, OH, and $C_{3-10}$ heterocyclyl, said alkyl, cycloalkyl, aryl, and heterocyclyl being optionally substituted with one to three members selected from $R^a$;

$R_2$ is H, $C_{1-6}$ alkyl, aryl, $C_{3-6}$ cycloalkyl, OH, $NO_2$, $NH_2$, or halogen;

$R_5$ is H, $C_{1-10}$ alkyl, $C_{3-6}$ cycloalkyl, $C_{1-6}$ alkoxy $C_{2-10}$ alkenyl, $C_{2-10}$ alkynyl, aryl, $C_{3-10}$ heterocyclyl, $C_{1-6}$ alkoxy$NR_7R_8$, halo, $NO_2$, OH, —$NH_2$, said alkyl, cycloalkyl, alkenyl, alkynyl, aryl, and heterocyclyl being optionally substituted with one to three members selected from $R^a$;

$R_{10}$ is H, or $C_{1-6}$ alkyl, $C_{1-6}$ alkyl$R_9$, $C_{5-10}$ aryl, $C_{3-10}$ heterocyclyl, $NHC_{1-6}$ alkyl$R_9$, said alkyl (where R is $C_{1-6}$ alkyl), aryl, heteroaryl and heterocyclyl being optionally substituted with from one to three members selected from $R^a$;

$R^a$ is $C_{1-10}$ alkyl, halogen, $NO_2$, CN, OR, $NR_7R_8$, aryl, or $C_{3-10}$ heterocyclyl;

R is H, $C_{1-6}$ alkyl or $C_{1-6}$ alkyl$R_9$;

$R_9$ is aryl or $C_{3-10}$ heterocyclyl, said aryl and heterocyclyl being optionally substituted with one to three members selected from $R^a$; and $R_7$ and $R_8$ are independently selected from the group consisting of:
H, $C_{1-10}$ alkyl, $C_{3-6}$ cycloalkyl, COR, aryl, and $C_{3-10}$ heterocyclyl, said alkyl, cycloalkyl, aryl, and heterocyclyl being optionally substituted with one to three members selected from $R^a$,
or $NR_7R_8$ can be taken together to form piperidinyl, pyrryl pyrrolidyl imidazolyl, or piperzinyl.

5. A compound in accordance with claim 4 wherein $R_{10}$ is H, $C_{1-10}$ alkyl, $C_{1-6}$ alkyl$R_9$, aryl, , or $C_{3-10}$ heterocyclyl, said alkyl, aryl, and heterocyclyl being optionally substituted with one to three members selected from $R^a$.

6. A compound in accordance with formula Ia:

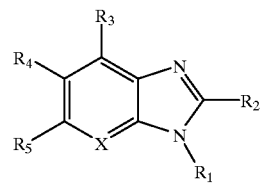

Ia or a pharmaceutically acceptable salt, hydrate or prodrug thereof,
wherein

X is C—H;

$R_1$ is phenyl, thienyl, or thiazolyl, said phenyl, thienyl and thiazolyl is optionally substituted with one to three members selected from $R^a$;

$R_2$ is H, $C_{1-6}$ alkyl, aryl, $C_{3-6}$ cycloalkyl, OH, $NO_2$, $NH_2$ or halo;

$R_3$ is selected from the group consisting of:
H, $C_{1-10}$ alkyl, $C_{3-6}$ cycloalkyl, aryl, halo, OH, and heterocyclyl, said alkyl, cycloalkyl, aryl, and heterocyclyl being optionally substituted with one to three members selected from $R^a$;

$R_4$ is selected from the group consisting of:
phenyl, pyridinyl, pyridinyl N-oxide, pyridinone, pyrimidinyl, and pyrimidinone, optionally substituted with one to three members selected from $R^a$, with the proviso that R₄ is not phenyl if R₁ is phenyl and that R₄ be substituted with OR or NR₇R₈ if R₄ is pyridyl when R₁ is phenyl;

R₅ is selected from the group consisting of:
H, C₁₋₁₀ alkyl, C₃₋₆ cycloalkyl, C₁₋₆ alkoxy, C₂₋₁₀ alkenyl, C₂₋₁₀ alkynyl, aryl, C₃₋₁₀ heterocyclyl, C₁₋₆ alkoxyNR₇R₈, halo, NO₂, OH, and —NH₂, said alkyl, cycloalkyl, alkenyl, alkynyl, aryl, and heterocyclyl being optionally substituted with one to three members selected from R$^a$, R$^a$ is: C₁₋₁₀ alkyl, halogen, NO₂, OR, R, CN, NR₇R₈, aryl, S(O)$_m$C₁₋₆alkyl, or heterocyclyl, wherein m is 0, 1, or 2;

R is: C₁₋₆ alkyl, optionally substituted with aryl or heterocyclyl, said aryl and heterocyclyl are optionally substituted with C₁₋₁₀ alkyl, halogen, NO₂, OC₁₋₆ alkyl, CN, NR₇R₈, aryl, or heterocyclyl; and R₇ and R₈ are independently selected from the group consisting of:
H, C₁₋₁₀ alkyl, C₃₋₆ cycloalkyl, (C=O)C₁₋₆ alkyl, aryl, and C₃₋₁₀ heterocyclyl, said alkyl, cycloalkyl, aryl, and heterocyclyl optionally substituted with one to three members selected from R$^a$,
or NR₇R₈ can be taken together to form piperidinyl, pyrryl, pyrrolidyl, imidazolyl, or piperzinyl.

7. A compound in accordance with claim 6 which is:
1-(2-morpholin-4-yl-ethyl)-4-(1-phenyl-1H-benzoimidazol-5-yl)-1H-pyridin-2-one, 1-(3-dimethylamino-propyl)-4-(1-phenyl-1H-benzoimidazol-5-yl)-1H-pyridin-2-one, 1-(1-methyl-piperidin-3-ylmethyl)-4-(1-phenyl-1H-benzoimidazol-5-yl)-1H-pyridin-2-one,
1-4-(1-phenyl-1H-benzoimidazol-5-yl)-1H-pyridin-2-one,
1-(2-dimethylamino-propyl)-4-(1-phenyl-1H-benzoimidazol-5-yl)-1H-pyridin-2-one,
1-(3-dimethylamino-2-methyl-propyl)-4-(1-phenyl-1H-benzoimidazol-5-yl)-1H-pyridin-2-one,
1-4-(1-phenyl-1H-benzoimidazol-5-yl)-1H-pyridin-2-one,
1-(3-piperidin-1-yl-propyl)-4-(1-thiophen-3-yl-1H-benzoinidazol-5-yl)-1H-pyridin-2-one,
1-(3-piperidin-1-yl-ethyl)-4-(1-thiophen-3-yl-1H-benzoinidazol-5-yl)-1H-pyridin-2-one,
1-(2-morpholin-4-yl-ethyl)-4-(1-thiophen-3-yl-1H-benzoimidazol-5-yl)-1H-pyridin-2-one,
1-(3-dimethylamino-propyl)-4-(1-thiophen-3-yl-1H-benzoimidazol-5-yl)-1H-pyridin-2-one,
1-(1-methyl-piperidin-3-ylmethyl)-4-(1-thiophen-3-yl-1H-benzoimidazol-5-yl)-1H-pyridin-2-one,
1-4-(1-thiophen-3-yl-1H-benzoimidazol-5-yl)-1H-pyridin-2-one,
1-(2-dimethylarnino-propyl)-4-(1-thiophen-3-yl-1H-benzoirmidazol-5-yl)-1H-pyridin-2-one,
1-(3-dimethylamino-2-methyl-propyl)-4-(1-thiophen-3-yl-1H-benzoimidazol-5-yl)-1H-pyridin-2-one,
1-4-(1-thiophen-3-yl-1H-benzoimidazol-5-yl)-1H-pyridin-2-one,
5-(1-phenyl-1H-benzoimnidazol-5-yl)-1-(3-piperidin-1-yl-propyl)-1H-pyridin-2-one,
5-(1-phenyl-1H-benzoimidazol-5-yl)-1-(3-piperidin-1-yl-ethyl)-1H-pyridin-2-one,
1-(2-morpholin-4-yl-ethyl)-5-(1-phenyl-1H-benzoimidazol-5-yl)-1H-pyridin-2-one,
1-(3-dimethylamino-propyl)-5-(1-phenyl-1H-benzoimidazol-5-yl)-1H-pyridin-2-one,
1-(1-methyl-piperidin-3-ylmethyl)-5-(1-phenyl-1H-benzoimidazol-5-yl)-1H-pyridin-2-one,
1-5-(1-phenyl-1H-benzoimidazol-5-yl)-1H-pyridin-2-one,
1-(2-dimethylamnino-propyl)-5-(1-phenyl-1H-benzoimidazol-5-yl)-1H-pyridin-2-one,
1-(3-dimethylamino-2-methyl-propyl)-5-(1-phenyl-1H-benzoimidazol-5-yl)-1H-pyridin-2-one,
1-[2-(4-cyano-piperidin-1-yl)-ethyl]-5-(1-phenyl-1H-benzoirnidazol-5-yl)-1H-pyridin-2-one,
1-(3-piperidin-1-yl-propyl)-5-(1-thiophen-3-yl-1H-benzoimidazol-5-yl)-1H-pyridin-2-one,
1-(3-piperidin-1-yl-ethyl)-5-(1-thiophen-3-yl-1H-benzoimidazol-5-yl)-1H-pyridin-2-one,
1-(2-morpholin-4-yl-ethyl)-5-(1-thiophen-3-yl-1H-benzoimidazol-5-yl)-1H-pyridin-2-one,
1-(3-dimethylamino-propyl)-5-(1-thiophen-3-yl-1H-benzoirnidazol-5-yl)-1H-pyridin-2-one,
1-(1-methyl-piperidin-3-ylmethyl)-5-(1-thiophen-3-yl-1H-benzoimnidazol-5-yl)-1H-pyridin-2-one,
1-5-(1-thiophen-3-yl-1H-benzoimidazol-5-yl)-1H-pyridin-2-one,
1-(2-dimethylamino-propyl)-5-(1-thiophen-3-yl-1H-benzoimidazol-5-yl)-1H-pyridin-2-one,
1-(3-dimethylarnino-2-methyl-propyl)-5-(1-thiophen-3-yl-1H-benzoirnidazol-5-yl)-1H-pyridin-2-one,
1-[2-(4-cyano-piperidin-1-yl)-ethyl]-5-(1-thiophen-3-yl-1H-benzoimidazol-5-yl)-1H-pyridin-2-one,
5-(1-phenyl-1H-benzoimidazol-5-yl)-1-(3-piperidin-1-yl-propyl)-1H-pyrimidin-2-one,
5-(1-phenyl-1H-benzoimidazol-5-yl)-1-(3-piperidin-1-yl-ethyl)-1H-pyrimidin-2-one,
1-(2-morpholin-4-yl-ethyl)-5-(1-phenyl-1H-benzoimidazol-5-yl)-1H-pyrimidin-2-one,
1-(3-dimethylarnino-propyl)-5-(1-phenyl-1H-benzoimnidazol-5-yl)-1H-pyrimidin-2-one,
1-(1-methyl-piperidin-3-ylmethyl)-5-(1-phenyl-1H-benzoimidazol-5-yl)-1H-pyrimidin-2-one,
1-[3-(4-methylpiperazin-1-yl)-propyl)]-5-(1-phenyl-1H-benzoimidazol-5-yl)-1H-pyrimidin-2-one,
1-(2-dimethylamnino-propyl)-5-(1-phenyl-1H-benzoimidazol-5-yl)-1H-pyrimidin-2-one,
1-(3-dimethylamino-2-methyl-propyl)-5-(1-phenyl-1H-benzoimidazol-5-yl)-1H-pyrimidin-2-one,
1-5-(1-phenyl-1H-benzoimidazol-5-yl)-1H-pyrimidin-2-one,
1-(3-piperidin-1-yl-propyl)-5-(1-thiophen-3-yl-1H-benzoimidazol-5-yl)-1H-pyrimidin-2-one,
1-(3-piperidin-1-yl-ethyl)-5-(1-thiophen-3-yl-1H-benzoimidazol-5-yl)-1H-pyrimidin-2-one,
1-(2-morpholin-4-yl-ethyl)-5-(1-thiophen-3-yl-1H-benzoimidazol-5-yl)-1H-pyrimi din-2-one,
1-(3-dimethylamino-propyl)-5-(1-thiophen-3-yl-1H-benzoimidazol-5-yl)-1H-pyrirnidin-2-one,
1-(1-methyl-piperidin-3-ylmethyl)-5-(1-thiophen-3-yl-1H-benzoimidazol-5-yl)-1H-pyrirnidin-2-one,
1-5-(1-thiophen-3-yl-1H-benzoimidazol-5-yl)-1H-pyrimidin-2-one,
1-(2-dimethylamino-propyl)-5-(1-thiophen-3-yl-1H-benzoimnidazol-5-yl)-1H-pyrimidin-2-one, 1-(3-dimethylamino-2-methyl-propyl)-5-(1-thiophen-3-yl-1H-benzoimidazol-5-yl)-1H-pyrimidin-2-one, 1-5-(1-thiophen-3-yl-1H-benzoimidazol-5-yl)-1H-pyrimidin-2-one, 4-(1-phenyl-1H-benzoimidazol-5-yl)-1-(3-piperidin-1-yl-propyl)-1H-pyrimidin-2-one, 4-(1-phenyl-1H-benzoimidazol-5-yl)-1-(3-piperidin-1-yl-ethyl)-1H-pyrimidin-2-one, 1-(2-morpholin-4-yl-ethyl)-4-( 1 -phenyl-1H-benzoimidazol-5-yl)-1H-pyrimidin-2-one, 1-(3-dimethylamino-propyl)-4-(1-phenyl-1H-benzoimidazol-5-yl)-1H-pyrirnidin-2-one, 1-(1-methyl-piperidin-3-ylmethyl)-4-(1-phenyl-1H-benzoimidazol-5-yl)-1H-pyrimidin-2-one, 1-4-(1-phenyl-1H-benzoirnidazol-5-yl)-1H-pyrimidin-2-one, 1-(2-dimethylarnino-propyl)-4-(1-phenyl-1H-benzoimidazol-5-yl)-1H-pyrirnidin-2-one, 1-(3-dimethylamino-2-methyl-propyl)-4-(1-phenyl-1H-benzoimidazol-5-yl)-1H-pyrimidin-2-one, 1-4-(1-phenyl-1H-benzoirnidazol-5-yl)-1H-pyrirnidin-2-one, 1-(3-piperidin-1-yl-propyl)-4-(1-thiophen-3-yl 1H-benzoimidazol-5-yl)- H-pyrimidin-2-one, 1-(3-piperidin-1-yl-ethyl)-4-(1-thiophen-3-yl-1H-benzoimidazol-5-yl)-1H-pyrimidin-2-one, 1-(2-morpholin-4-yl-ethyl)-4-(1-thiophen-3-yl-1H-benzoirnidazol-5-yl)-1H-pyrimidin-2-one, 1-(3-dimethylamino-propyl-4-(1-thiophen-3-yl-1 H-benzoimidazol-5-yl)-1H-pyrimidin-2-one, 1-(1-methyl-piperidin-3-ylmethyl)-4-(1-thiophen-3-yl-1H-benzoimidazol-5-yl)-1H-pyrimidin-2-one, 1-4-(1-thiophen-3-yl-1H-benzoimidazol-5-yl)-1H-pyrimidin-2-one, 1-(2-dimethylamino-propyl)4-(1-thiophen-3-yl-1H-benzoimidazol-5-yl)-1H-pyrimidin-2-one, 1-(3-dimethylamino-2-methyl-propyl)-4-(1-thiophen-3-yl-1H-benzoimidazol-5-yl)-1H-pyrimidin-2-one, 1-4-(1-thiophen-3-yl-1H-benzoimidazol-5-yl)-1H-pyrimidin-2-one or a pharmaceutically acceptable salt, hydrate or prodrug thereof.

8. A pharmaceutical composition which is comprised of a compound in accordance with claim 6 and a pharmaceutically acceptable carrier.

9. A method of treating cancer by inhibiting VEGF receptor tyrosine kinase signal transduction in a mammalian patient in need of such treatment which is comprised of administering to said patient a therapeutically effective amount of a compound of claim 6.

10. A method of treating cancer in accordance with claim 9 wherein the cancer is selected from cancers of the brain, genitourinary tract, lymphatic system, stomach, larynx and lung.

11. A method in accordance with claim 9 wherein the cancer comprises histiocytic lymphoma, lung adenocarcinoma, small cell lung cancers, pancreatic cancer, glioblastoma and breast carcinoma.

12. A method of treating a disease in which neoangiogenesis is implicated by inhibiting VEGF receptor tyrosine kinase signal transduction, which is comprised of administering to a mammalian patient in need of such treatment a therapeutically effective amount of a compound of claim 6.

13. A method in accordance with claim 12 wherein the disease is an ocular disease.

14. A method of treating retinal vascularization by inhibiting VEGF receptor tyrosine kinase signal transduction which is comprised of administering to a mammalian patient in need of such a treatment a therapeutically effective amount of a compound of claim 6.

15. A method of treating diabetic retinopathy by inhibiting VEGF receptor tyrosine kinase signal transduction which is comprised of administering to a mammalian patient in need of such treatment a therapeutically effective amount of a compound of claim 8.

16. A method of treating age-related macular degeneration by inhibiting VEGF receptor tyrosine kinase signal transduction which is comprised of administering to a mammalian patient in need of such treatment a therapeutically effective amount of a compound of claim 8.

17. A method of treating inflammatory diseases by inhibiting VEGF receptor tyrosine kinase signal transduction which is comprised of administering to a mammalian patient in need of such treatment a therapeutically effective amount of a compound of claim 8.

18. A method according to claim 17 wherein the inflammatory disease is selected from rheumatoid arthritis, psoriasis, contact dermatitis and delayed hypersensitivity reactions.

19. A method for inhibiting tyrosine kinase of the endothelial cell growth factor receptor which comprises administering to a mammalian patient in need of such treatment a therapeutically effective amount of a compound of claim 6.

20. A compound in accordance with claim 6 wherein $R_3$ is selected from the group consisting of:

H, $C_{1-10}$ alkyl, aryl, and $C_{3-10}$ heterocyclyl, said alkyl, aryl, and heterocyclyl being optionally substituted with one to three members selected from $R^a$; and $R_5$ is selected from the group consisting of:

H, $C_{1-10}$ alkyl, $C_{3-6}$ cycloalkyl, aryl, $C_{3-10}$ heterocyclyl, $C_{1-6}$ alkoxyNR$_7$R$_8$, NO$_2$, OH, and —N$_2$, said alkyl, cycloalkyl, aryl, and heterocyclyl optionally substituted with one to three members selected from $R^a$.

21. A compound which is:

1-phenyl-5-(4-methoxyphenyl)benzimidazole, 1-phenyl-5-(4-(2-(1-piperidinyl)ethoxy)phenyl)benzimidazole, 1-(2-thiazoyl)-5-(4-(3-(1-piperidinyl)propyl)phenyl)benzimidazole, 1-(3-thiophenyl)-5-(4-(3-(1-piperidinyl)propyl)phenyl)benzimidazole, 1-phenyl-5-1H-benzimidazole, 1-(4-cyanophenyl)-5-1H-benzimidazole, 1-phenyl-5-1H-benzimidazole, 1-(3-cyanophenyl)-5-1H-benzimidazole, 1-(3-thiophene)-5-1H-benzimidazole, -(2-piperidin-1-yl-ethyl)-amine, -(2-morpholin-1-yl-ethyl)-amine, 4-(1-phenyl-1H-benzoimidazol-5-yl)-1-(3-piperidin-1-yl-propyl)-1H-pyridin-2-one, 4-(1-phenyl-1H-benzoimidazol-5-yl)-1-(3-piperidin-1-yl-ethyl)-1H-pyridin-2-one, 1-(3-pyridyl)-5-(4-(2-(1-piperidinyl)ethoxy)phenyl)benzimidazole, 1-(4-pyridyl)-5-(4-(2-(1-piperidinyl)ethoxy)phenyl)benzimidazole, 1-(3-pyridyl)-5-1H-benzimidazole, or 1-(4-pyridyl)-5-1H-benzinidazole or a pharmaceutically acceptable salt, hydrate or prodrug thereof.

* * * * *

UNITED STATES PATENT AND TRADEMARK OFFICE
CERTIFICATE OF CORRECTION

PATENT NO.    : 6,162,804
DATED         : December 19, 2000
INVENTOR(S)   : Mark T. Bilodeau, April M. Cunningham, Randall W. Hungate and Timothy J. Koester It is certified that error appears in the above-identified patent and that said Letters Patent is hereby corrected as shown below:

Column 35, claim 1,
Line 28, should read as follows -- is pyridyl when $R_1$ is phenyl; -- .

Column 37, claim 7, line 28 through column 39, line 43,
Should read as follows:
1-(2-morpholin-4-yl-ethyl)-4-(1-phenyl-lH-benzoimidazol-5-yl)-1H-pyridin-2-one,
1-(3-dimethylamino-propyl)-4-(1-phenyl-1H-benzoimidazol-5-yl)-1H-pyridin-2-one,
1-(1-methyl-piperidin-3-ylmethyl)-4-(1-phenyl-lH-benzoimidazol-5-yl)-1H-pyridin-2-one,
1-[3-(4-methylpiperazin-l-yl)-propyl)]-4-(1-phenyl-lH-benzoimidazol-5-yl)-1H-pyridin-2-one,
1-(2-dimethylamino-propyl)-4-(1-phenyl-lH-benzoimidazol-5-yl)-1H-pyridin-2-one,
1-(3-dimethylamino-2-methyl-propyl)-4-(1-phenyl-lH-benzoimidazol-5-yl)-1H-pyridin-2-one,
1-[2-(4-cyano-piperidin-l-yl)-ethyl]-4-(1-phenyl-1H-benzoimidazol-5-yl)-1H-pyridin-2-one,
1-(3-piperidin-1-yl-propyl)-4-(1-thiophen-3-yl-1H-benzoimidazol-5-yl)-1H-pyridin-2-one,
1-(3-piperidin-1-yl-ethyl)-4-(1-thiophen-3-yl-1H-benzoimidazol-5-yl)-1H-pyridin-2-one,
1-(2-morpholin-4-yl-ethyl)-4-(1-thiophen-3-yl- lH-benzoimidazol-5-yl)-lH-pyridin-2-one,
1-(3-dimethylamino-propyl)-4-(1-thiophen-3-yl-lH-benzoimidazol-5-yl)-1H-pyridin-2-one,
1-(1-methyl-piperidin-3-ylmethyl)-4-(1-thiophen-3-yl-1H-benzoimidazol-5-yl)-1H-pyridin-2-one,
1-[3-(4-methylpiperazin-1-yl)-propyl)]-4-(1-thiophen-3-yl- lH-benzoimidazol-5-yl)-1H-pyridin-2-one,
1-(2-dimethylamino-propyl)-4-(1-thiophen-3-yl-1H-benzoimidazol-5-yl)-1 H-pyridin-2-one,
1-(3-dimethylamino-2-methyl-propyl)-4-(1-thiophen-3-yl-1 H-benzoimidazol-5-yl)-1H-pyridin-2-one,
1-[2-(4-cyano-piperidin-l-yl)-ethyl]-4-(1-thiophen-3-yl-lH-benzoimidazol-5-yl)-1H-pyridin-2-one,
5-(1-phenyl-1H-benzoimidazol-5-yl)-1-(3-piperidin-1-yl-propyl)-1H-pyridin-2-one,
5-(1-phenyl-1H-benzoimidazol-5-yl)-1-(3-piperidin-l-yl-ethyl)-1H-pyridin-2-one,
1-(2-morpholin-4-yl-ethyl)-5-(1-phenyl-lH-benzoimidazol-5-yl)-1H-pyridin-2-one,
1-(3-dimethylamino-propyl)-5-(1-phenyl-lH-benzoimidazol-5-yl)-1H-pyridin-2-one,
1-(1-methyl-piperidin-3-ylmethyl)-5-(1-phenyl-1 H-benzoimidazol-5-yl)-1 H-pyridin-2-one,
1-[3-(4-methylpiperazin-1-yl)-propyl)]-5-(1-phenyl-lH-benzoimidazol-5-yl)-1H-pyridin-2-one,
1-(2-dimethylamino-propyl)-5-(1-phenyl-1H-benzoimidazol-5-yl)-1H-pyridin-2-one,
1-(3-dimethylamino-2-methyl-propyl)-5-(1-phenyl-lH-benzoimidazol-5-yl)-1H-pyridin-2-one,

UNITED STATES PATENT AND TRADEMARK OFFICE
CERTIFICATE OF CORRECTION

PATENT NO. : 6,162,804
DATED : December 19, 2000
INVENTOR(S) : Mark T. Bilodeau, April M. Cunningham, Randall W. Hungate and Timothy J. Koester It is certified that error appears in the above-identified patent and that said Letters Patent is hereby corrected as shown below:

1-[2-(4-cyano-piperidin-1-yl)-ethyl]-5-(1-phenyl-1H-benzoimidazol-5-yl)-1H-pyridin-2-one,
1-(3-piperidin-1-yl-propyl)-5-(1-thiophen-3-yl-1H-benzoimidazol-5-yl)-1H-pyridin-2-one,
1-(3-piperidin-1-yl-ethyl)-5-(1-thiophen-3-yl-1H-benzoimidazol-5-yl)-1H-pyridin-2-one,
1-(2-morpholin-4-yl-ethyl)-5-(1-thiophen-3-yl-1H-benzoimidazol-5-yl)-1 H-pyridin-2-one,
1-(3-dimethylamino-propyl)-5-(1-thiophen-3-yl-1H-benzoimidazol-5-yl)-1H-pyridin-2-one,
1-(1-methyl-piperidin-3-ylmethyl)-5-(1-thiophen-3-yl-1H-benzoimidazol-5-yl)-1H-pyridin-2-one,
1-[3-(4-methylpiperazin-1-yl)-propyl)]-5-(1-thiophen-3-yl-1H-benzoimidazol-5-yl)-1 H-pyridin-2-one,
1-(2-dimethylamino-propyl)-5-(1-thiophen-3-yl-1 H-benzoimidazol-5-yl)-1H-pyridin-2-one,
1-(3-dimethylamino-2-methyl-propyl)-5-(1-thiophen-3-yl-1H-benzoimidazol-5-yl)-1H-pyridin-2-one,
1-[2-(4-cyano-piperidin-1-yl)-ethyl]-5-(1-thiophen-3-yl-lH-benzoimidazol-5-yl)-1H-pyridin 2-one,
5-(1-phenyl-1H-benzoimidazol-5-yl)-1-(3-piperidin-1-yl-propyl)-1H-pyrimidin-2-one,
5-(1-phenyl-1H-benzoimidazol-5-yl)-1-(3-piperidin-1-yl-ethyl)-1H-pyrimidin-2-one,
1-(2-morpholin-4-yl-ethyl)-5-(1-phenyl-lH-benzoimidazol-5-yl)-1H-pyrimidin-2-one,
1-(3-dimethylamino-propyl)-5-(1-phenyl-1 H-benzoimidazol-5-yl)-1H-pyrimidin-2-one,
1-(1-methyl-piperidin-3-ylmethyl)-5-(1-phenyl-1H-benzoimidazol-5-yl)-1H-pyrimidin-2-one,
1-[3-(4-methylpiperazin-1-yl)-propyl)]-5-(1-phenyl-1H-benzoimidazol-5-yl)-1H-pyrimidin-2-one,
1-(2-dimethylamino-propyl)-5-(1-phenyl-1H-benzoimidazol-5-yl)-1H-pyrimidin-2-one,
1-(3-dimethylamino-2-methyl-propyl)-5-(1-phenyl-lH-benzoimidazol-5-yl)-1H-pyrimidin-2-one,
1-[2-(4-cyano-piperidin-l-yl)-ethyl]-5-(1-phenyl-lH-benzoimidazol-5-yl)-1H-pyrimidin-2-one,
1-(3-piperidin-l-yl-propyl)-5-(1-thiophen-3-yl-lH-benzoimidazol-5-yl)-1H-pyrimidin-2-one,
1-(3-piperidin-l-yl-ethyl)-5-(1-thiophen-3-yl-1H-benzoimidazol-5-yl)-1H-pyrimidin-2-one,
1-(2-morpholin-4-yl-ethyl)-5-(1-thiophen-3-yl-lH-benzoimidazol-5-yl)-1H-pyrimidin-2-one,
1-(3-dimethylamino-propyl)-5-(1-thiophen-3-yl-lH-benzoimidazol-5-yl)-1H-pyrimidin-2-one,
1-(1-methyl-piperidin-3-ylmethyl)-5-(1-thiophen-3-yl-lH-benzoimidazol-5-yl)-1H-pyrimidin-2-one,
1-[3-(4-methylpiperazin-1-yl)-propyl)]-5-(1-thiophen-3-yl-lH-benzoimidazol-5-yl)-1H-pyrimidin-2-one,
1-(2-dimethylamino-propyl)-5-(1-thiophen-3-yl-lH-benzoimidazol-5-yl)-1H-pyrimidin-2-one,

UNITED STATES PATENT AND TRADEMARK OFFICE
CERTIFICATE OF CORRECTION

PATENT NO. : 6,162,804
DATED : December 19, 2000
INVENTOR(S) : Mark T. Bilodeau, April M. Cunningham, Randall W. Hungate and Timothy J. Koester It is certified that error appears in the above-identified patent and that said Letters Patent is hereby corrected as shown below:

1-(3-dimethylamino-2-methyl-propyl)-5-(1-thiophen-3-yl-lH-benzoimidazol-5-yl)-1H-pyrimidin-2-one,
1-[2-(4-cyano-piperidin-1-yl)-ethyl]-5-(1-thiophen-3-yl-1H-benzoimidazol-5-yl)-1H-pyrimidin-2-one,
4-(1-phenyl-1H-benzoimidazol-5-yl)-1-(3-piperidin-1-yl-propyl)-1H-pyrimidin-2-one,
4-(1-phenyl-lH-benzoimidazol-5-yl)-1-(3-piperidin-1-yl-ethyl)-1H-pyrimidin-2-one,
1-(2-morpholin-4-yl-ethyl)-4-(1-phenyl-lH-benzoimidazol-5-yl)-1H-pyrimidin-2-one,
1-(3-dimethylamino-propyl)-4-(1-phenyl-1H-benzoimidazol-5-yl)-1H-pyrimidin-2-one,
1-(1-methyl-piperidin-3-ylmethyl)-4-(1-phenyl-lH-benzoimidazol-5-yl)-1H-pyrimidin-2-one,
1-[3-(4-methylpiperazin-1-yl)-propyl)]-4-(1-phenyl-1H-benzoimidazol-5-yl)-1H-pyrimidin-2-one,
1-(2-dimethylamino-propyl)-4-(1-phenyl-1 H-benzoimidazol-5-yl)-1H-pyrimidin-2-one,
1-(3-dimethylamino-2-methyl-propyl)-4-(1-phenyl-lH-benzoimidazol-5-yl)-1H-pyrimidin-2-one,
1-[2-(4-cyano-piperidin-1-yl)-ethyl]-4-(1-phenyl-lH-benzoimidazol-5-yl)-1H-pyrimidin-2-one,
1-(3-piperidin-1-yl-propyl)-4-(1-thiophen-3-yl-lH-benzoimidazol-5-yl)-1H-pyrimidin-2-one,
1-(3-piperidin-1-yl-ethyl)-4-(1-thiophen-3-yl-1H-benzoimidazol-5-yl)-1H-pyrimidin-2-one,
1-(2-morpholin-4-yl-ethyl)-4-(1-thiophen-3-yl-lH-benzoimidazol-5-yl)-1H-pyrimidin-2-one,
1-(3-dimethylamino-propyl)-4-(1-thiophen-3-yl-lH-benzoimidazol-5-yl)-1 H-pyrimidin-2-one,
1-(1-methyl-piperidin-3-ylmethyl)-4-(1-thiophen-3-yl-1H-benzoimidazol-5-yl)-1H-pyrimidin-2-one,
1-[3-(4-methylpiperazin-1-yl)-propyl)]-4-(1-thiophen-3-yl-1H-benzoimidazol-5-yl)-1H-pyrimidin-2-one,
1-(2-dimethylamino-propyl)-4-(1-thiophen-3-yl-1H-benzoimidazol-5-yl)-1H-pyrimidin-2-one,
1-(3-dimethyllamino-2-methyl-propyl)-4-(1-thiophen-3-yl-1H-benzoimidazol-5yl)-1H-Pyrimidin-2-one,
1-[2-(4-cyano-piperidin-1-yl)-ethyl]-4-(1-thiophen-3-yl-1H-benzoimidazol-5-yl)-1H-pyrimidin-2-one or a pharmaceutically acceptable salt, hydrate or prodrug thereof.

Column 40, claim 20,
Line 34, should read as follows:
-- -NH$_2$, said alkyl, cycloalkyl, aryl, and heterocyclyl --.

UNITED STATES PATENT AND TRADEMARK OFFICE
CERTIFICATE OF CORRECTION

PATENT NO. : 6,162,804
DATED : December 19, 2000
INVENTOR(S) : Mark T. Bilodeau, April M. Cunningham, Randall W. Hungate and Timothy J. Koester It is certified that error appears in the above-identified patent and that said Letters Patent is hereby corrected as shown below:

Column 40, claim 21,
Lines 46, 51, 63, and 64, respectively, should read as follows,
-- 1-phenyl-5-[5-(2-piperidin-1-yl-ethoxy)-pyridin-2-yl]-1H-benzimidazole, --
-- 1-(3-thiophene)5-[6-(2-piperidin-1-yl-ethoxy)-pyridin-3-yl]-1H-benzimidazole, --
-- 1-(3-pyridyl)-5-[6-(2-piperidin-1-yl-ethoxy)-pyridin-3-yl]-1H-benzimidazole, or --
-- 1-(4-pyridyl)-5-[6-(2-piperidin-1-yl-ethoxy)-pyridin-3-yl]-1H-benzimidazole or a --.

Signed and Sealed this

Eighteenth Day of December, 2001

Attest:

*Attesting Officer*

JAMES E. ROGAN
*Director of the United States Patent and Trademark Office*